US007295305B2

(12) United States Patent
Yoshida et al.

(10) Patent No.: US 7,295,305 B2
(45) Date of Patent: *Nov. 13, 2007

(54) METHOD AND ITS APPARATUS FOR INSPECTING A PATTERN

(75) Inventors: Minoru Yoshida, Yokohama (JP); Shunji Maeda, Yokohama (JP); Hidetoshi Nishiyama, Fujisawa (JP)

(73) Assignee: Hitachi High-Technologies Corporation, Tokyo (JP)

(*) Notice: Subject to any disclaimer, the term of this patent is extended or adjusted under 35 U.S.C. 154(b) by 198 days.

This patent is subject to a terminal disclaimer.

(21) Appl. No.: 10/914,115

(22) Filed: Aug. 10, 2004

(65) Prior Publication Data

US 2005/0062963 A1 Mar. 24, 2005

(30) Foreign Application Priority Data

Sep. 18, 2003 (JP) ............................ 2003-325526

(51) Int. Cl.
*G01N 21/00* (2006.01)

(52) U.S. Cl. .................................................. 356/237.5

(58) Field of Classification Search ............. 356/237.4, 356/237.5

See application file for complete search history.

(56) References Cited

U.S. PATENT DOCUMENTS 5,774,222 A * 6/1998 Maeda et al. ............... 356/394
6,031,607 A * 2/2000 Miyazaki ................. 356/237.1
6,084,716 A * 7/2000 Sanada et al. .............. 359/629
6,288,780 B1 * 9/2001 Fairley et al. ........... 356/237.1
6,369,888 B1 * 4/2002 Karpol et al. ............ 356/237.5
6,621,571 B1 * 9/2003 Maeda et al. ............ 356/237.5
6,900,888 B2 * 5/2005 Yoshida et al. .......... 356/237.4

FOREIGN PATENT DOCUMENTS

| | | |
|---|---|---|
| JP | 59-226317 | 12/1984 |
| JP | 62-231924 | 10/1987 |
| JP | 07-318326 | 12/1995 |
| JP | 08-320294 | 12/1996 |
| JP | 10-078668 | 3/1998 |

* cited by examiner

*Primary Examiner*—Tarifur Chowdhury
*Assistant Examiner*—Isiaka O Akanbi
(74) *Attorney, Agent, or Firm*—Antonelli, Terry, Stout & Kraus, LLP.

(57) ABSTRACT

An apparatus for inspecting a defect, has a light source; a rotating diffuser plate for reducing coherence of light emitted from the light source after its light intensity was adjusted and its illumination range is formed; oscillating mirrors that variably change the beam whose coherence was reduced on a pupil, irradiates it onto a wafer, and forms an image thereof. An image sensor images the wafer by focusing reflected light from the wafer and detects an image signal; a camera observes the detected image; and an image processing unit detects a defect of a pattern formed on the wafer based on the detected image signal. Thus, conditions for illuminating the sample can be changed variably in an arbitrary and easy manner, and a more minute defect can be detected with high sensitivity by changing transmissivity and phase conditions of a pupil filter on the detection side.

26 Claims, 31 Drawing Sheets

1: Wafer
4: Illumination light source
14,19: Oscillating mirror
29: Rotating diffuser plate
32: Observation camera
35: Image sensor
37: Image processing unit 1: Wafer
4: Illumination light source
14, 19: Oscillating mirror
29: Rotating diffuser plate
32: Observation camera
35: Image sensor
37: Image processing unit (a)

(b)

(a)

(b)

METHOD AND ITS APPARATUS FOR INSPECTING A PATTERN

BACKGROUND OF THE INVENTION

This invention relates to pattern inspection for detection of defects, such as a short circuit and the breaking of wire, and foreign matter. Specifically, the invention relates to a pattern inspection apparatus and method for use in the manufacture of a semiconductor wafer, a liquid crystal display, and a photomask. Note that in the following description, the term "defect" includes foreign matter, and "a pattern to be inspected" will be referred to as an "inspection pattern" hereinafter.

As far as the present inventors are aware, regarding pattern inspection technology for detecting a defect in an inspection pattern, the following technologies have been developed.

JP-A No. 318326/1995 discloses an inspection apparatus in which an image of an inspection pattern is detected by an imaging element, such as an image sensor, while the inspection pattern is being moved, and a detected image signal and an image signal that represents the detected image signal delayed by a predetermined time are compared in terms of gray-scale value, whereby a nonconformity is recognized as a defect.

Further, JP-A No. 320294/1996 discloses a technique for defect inspection of an inspection pattern. According to this technique, in inspection patterns of a semiconductor wafer in which a region of high pattern density, such as a memory mat part, and a region of low pattern density, such as a peripheral circuit, are mixed in a single chip, a digital image signal obtained by A/D converting the detected image signal is subjected to gray-scale translation. This gray-scale translated image signal is then compared to an image signal that was subjected to gray-scale translation and is to be compared while the two are aligned so that the brightness or contrast between the high density region and the low density region of the inspection pattern becomes a predetermined relationship according to a frequency distribution of brightness on a detected image, and thereby a minute defect can be detected with high accuracy.

Moreover, a method of inspecting the pattern of a photomask is disclosed by JP-A No. 78668/1998. JP-A No. 78668/1998 discloses a technique in which a UV laser beam, such as an excimer laser beam, is used as a light source, the mask is illuminated uniformly with the UV light whose coherence was reduced by rotating a diffuser plate inserted into an optical path, features are calculated from obtained image data of the mask, and the quality of the photomask is judged. Moreover, a projection aligner using an excimer laser is disclosed in JP-A No. 226317/1984, JP-A No. 231924/1987, etc.

On the other hand, the present inventors have examined the various techniques used in pattern inspection technology for detecting a defect in an inspection pattern, as mentioned above, and have come to the following conclusions.

For example, in LSI manufacture in recent years, a circuit pattern formed on a wafer has become more minute, having been reduced down to 200 nm or less in pattern width, in response to the need for a high degree of integration, which has come up to the resolution limit of the optical system for performing pattern inspection. For this reason, enhancement of the NA of the objective lens for inspection to higher values and the application of super resolution technology are being advanced.

However, enhancement of the NA of the objective lens for inspection to higher values has reached a physical limit. Therefore, making the wavelength used for the inspection shorter toward the region of ultraviolet light (UV light) and far ultraviolet light (DUV light) is an essential approach.

In the inspection, since it is necessary to perform inspection at high speed, a method of scanning a narrow-focused laser beam on the sample cannot be used. Conversely, if the laser beam is expanded to the whole visual field for illumination, speckle occurs and overshoot/undershoot called ringing occurs at the edge part of a circuit pattern; therefore, an excellent quality of image production cannot be obtained.

On the other hand, the inspection device has been changing, and the structure of the inspection pattern has become complex and diversified, such as memory products that are formed with repeated patterns and logic products that are formed with non-repeated patterns. Therefore, it has become difficult to find a targeted defect surely.

SUMMARY OF THE INVENTION

An object of the present invention is to provide an apparatus and method for inspecting a pattern for defects that is capable of detecting a minute circuit pattern with high resolution and at high speed and which detects a defect by appropriately changing the illumination conditions corresponding to the structure of the device to be inspected.

Another object of the present invention is to provide a method for manufacturing a semiconductor device in which a superfine semiconductor device can be manufactured using the apparatus and method for inspecting a pattern defect.

One aspect of the present invention is directed to an apparatus for inspecting a pattern defect comprising: an illumination light source; light-intensity adjusting means for adjusting the light intensity from the illumination light source (ND filter etc.); illumination-range forming means for forming an illumination range of the illumination light that was adjusted by the light-intensity adjusting means (homogenizer etc.); coherence reducing means for reducing the coherence of the illumination light emitted from the illumination-range forming means (rotating diffuser plate etc.); illumination means for changing the shape of the beam whose coherence was reduced by the coherence reducing means on the pupil variably and irradiating it onto a sample to form an image (oscillating mirrors etc.); focusing means for focusing reflected light from the sample into an image (imaging lens etc.); diffracted-light controlling means for controlling diffracted light of the imaging means (polarizing element etc.); image detecting means for imaging the sample formed by the imaging means and detecting an image signal (image sensor etc.); observation means for observing a detection image detected by the image detecting means; and defect detecting means for detecting a defect of the pattern formed on the sample based on information on the detection image signal detected by the image detecting means (image processing unit).

In another aspect of the invention, an inspection method includes irradiating ultraviolet light whose coherence was reduced onto a wafer having a diameter as much as 300 mm, imaging the wafer thus irradiated to detect an image of the wafer, and processing the detected image of the wafer to detect a defect not more than 100 nm in size of the pattern formed on the wafer at a throughput of three sheets per hour or more. That is, it is characterized by inspecting a pattern of a design rule of 70 nm or less in the manufacture of a semiconductor device.

According to this invention, since the illumination conditions under which the sample is illuminated can be changed variably in an arbitrary and easy manner, inspection under optimal illumination conditions becomes possible in various steps, and, further, a defect that cannot be detected under a normal illumination can be made obvious. Furthermore, this invention provides an effect in which, by changing the transmissivity and phase conditions of a pupil filter on the detection side, information of a defect part having been made obvious can be further enhanced, so that a more minute defect can be detected with high sensitivity.

These and other objects, features and advantages of the invention will be apparent from the following more particular description of preferred embodiments of the invention, as illustrated in the accompanying drawings.

DESCRIPTION OF THE PREFERRED EMBODIMENTS

Figure 1:
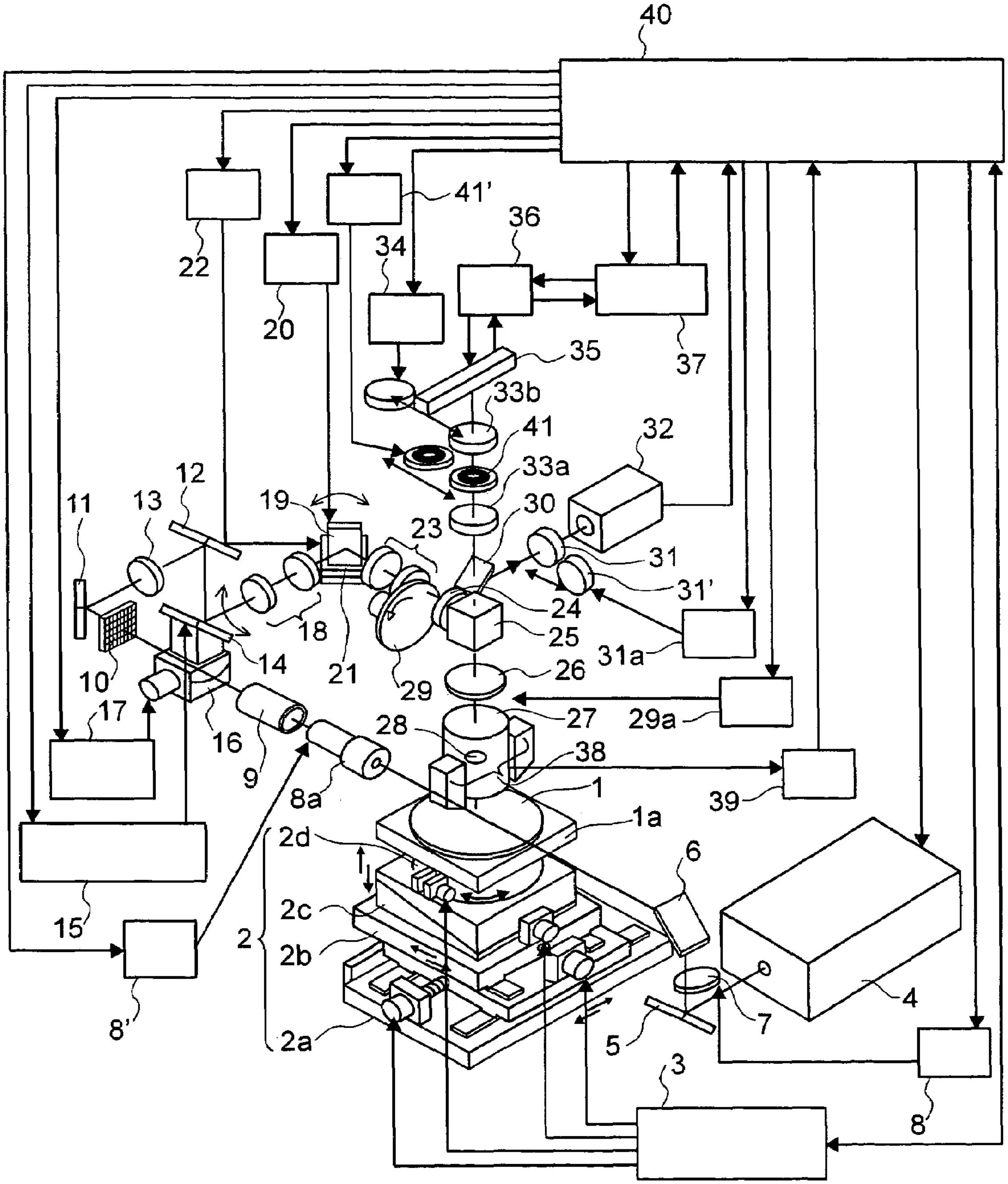
FIG. 1 is a block diagram showing one embodiment of an apparatus for inspecting an inspection pattern according to this invention.

Hereafter, various embodiments of an apparatus for inspecting a pattern and a method for the same according to this invention will be described in detail with reference to the drawings. Note that in all of the figures, members each having the same function are designated with the same reference numeral, and a repeated explanation thereof is omitted.

FIG. 1 is a view showing one embodiment of the apparatus for inspecting a pattern according to this invention. In this embodiment, a wafer 1 is fixed to the uppermost surface of a stage 2 by a wafer chuck 1*a*, for example, by vacuum suction etc. The stage 2 is composed of a Y stage 2*a*, an X stage 2*b*, a θ stage 2*c*, and a Z stage 2*d*. The wafer chuck 1*a* is fixed to the Z stage 2*d*. The X stage 2*b* is capable of constant speed movement. The Y stage 2*a* is capable of stepwise movement. The θ stage 2*c* is capable of rotating the wafer chuck 1*a* and, hence, is capable of correcting the propagation direction of the stage 2 and the tilt of the wafer 1. The Z stage 2*d* is capable of moving the wafer 1 vertically. Each movement can be controlled by a stage control circuit 3.

An illumination light source 4 is provided in the form of an ultraviolet or far-ultraviolet laser light source having a wavelength of, for example, 355 nm or 266 nm, for illuminating the surface of the wafer 1. This laser light source is made up of an apparatus that converts the wavelength of a solid-sate YAG laser by means of a nonlinear optical crystal etc. to generate a third harmonic (355 nm) of the fundamental wave or a fourth harmonic (266 nm) thereof. Alternatively, a laser light source having a wavelength of 193 nm, 195 nm, or 248 nm may be used. Alternatively, if there is a laser light source having a wavelength of 100 nm or shorter, such a laser light source may be used. In this case, the resolution will be increased even further because of the shorter wavelength. Moreover, the oscillation mode of the laser may be continuous oscillation or pulsed oscillation. However, in the case where the stage 2 is moved continuously to detect an image from the wafer 1, continuous oscillation is preferable. Any pulsed laser light source whose repetition frequency is high can be treated in a similar manner as a continuous oscillation laser.

Figure 2:
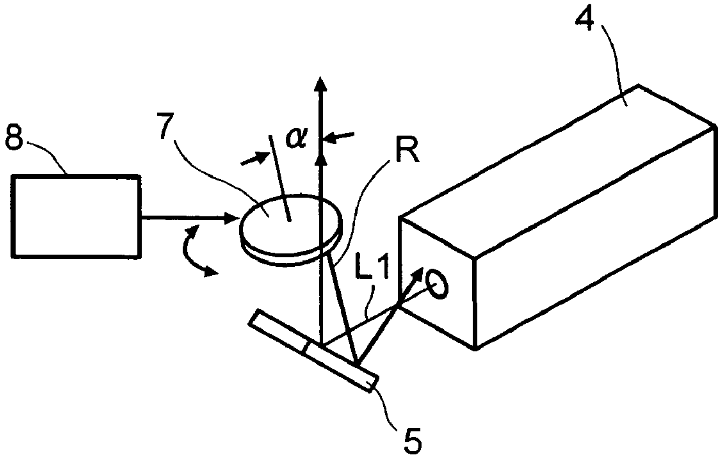
FIG. 2(*a*) is a perspective view and FIG. 2(*b*) is a graph illustrating a ND filter mechanism according to this invention.
Figure 2:
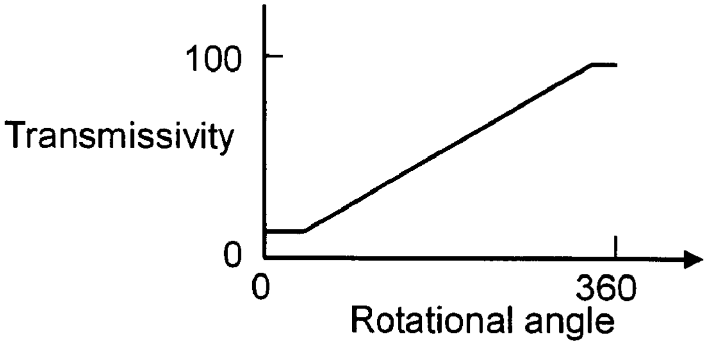

A beam from the illumination light source 4 is guided to an illumination optical system by mirrors 5, 6. An ND filter 7 can adjust the light intensity to be led to the illumination optical system. The ND filter 7 can be driven according to an instruction of an ND filter control circuit 8 by a known method. Referring to FIGS. 2(*a*) and 2(*b*), the ND filter 7 will be described. FIG. 2(*a*) is a view showing the arrangement of the ND filter, and FIG. 2(*b*) is a graph showing a relationship between the transmissivity (light intensity) and the rotational angle of the ND filter. The beam from the illumination light source 4 is emitted at the maximum output for stabilization of the laser. Therefore, it is necessary to set up the light intensity required for inspection. In FIG. 2(*a*), the beam from the illumination light source 4 is reflected by a mirror 5, and passes through the ND filter 7. At this time, if the ND filter 7 makes a right angle with the beam, its reflected light will be reflected by the mirror 5 again and return to the inside of the illumination light source 4. Then, the laser light will interfere with the reflected light in the resonator of the illumination light source 4, which will make the laser output unstable.

For this reason, the ND filter 7 is inclined to the beam by an angle of α. The angle of α may be any angle unless the beam R reflected by the ND filter 7 does not return directly to the outgoing window of the laser of the illumination light source 4. As the ND filter 7, for example, a filter whose transmissivity varies depending on the rotational angle as shown in FIG. 2(*b*) is used. Incidentally, the ND filter 7 can be rotated by a known method, and can be fixed at a predetermined angle by the ND filter control circuit 8. Needless to say, if several kinds of fixed ND filters whose transmissivities are previously set are provided and one of them is switched over, a similar effect can be obtained. Note that, also in this state, the fixed ND filter is disposed with its normal inclined to the beam by an angle of α.

Figure 3:
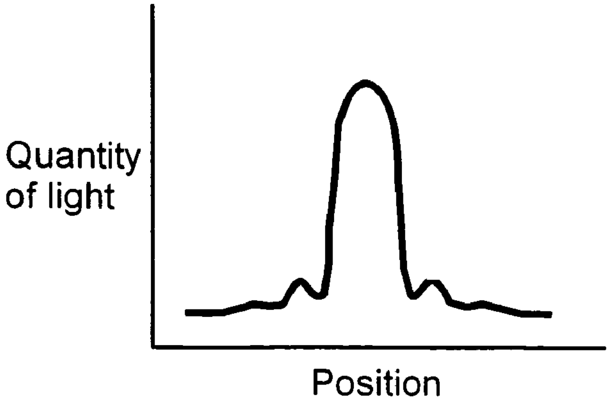
FIG. 3 is a graph illustrating the intensity distribution of a laser beam according to this invention.
Figure 4:
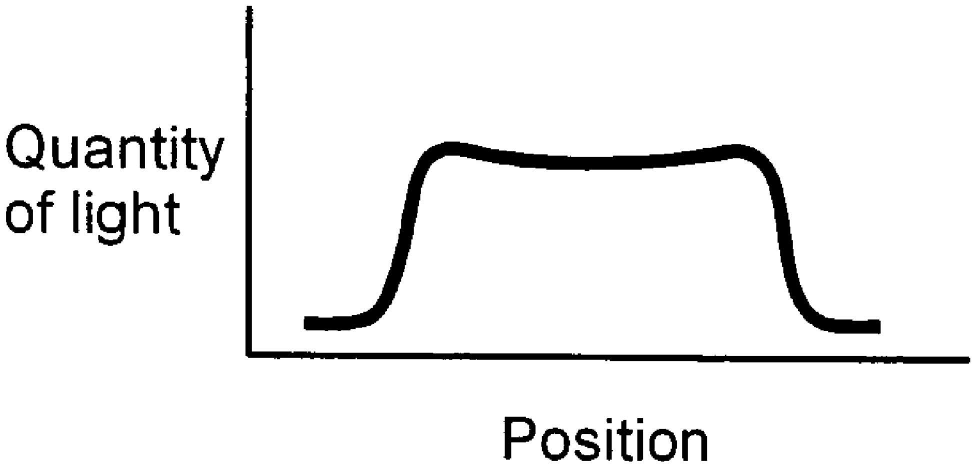
FIG. 4 is a graph illustrating the intensity distribution of a beam after being transmitted through a beam shaper according to this invention.

Next, the beam from the illumination light source 4 is expanded by a beam expander 8*a*, and it passes through a beam shaper 9. FIG. 3 shows a general intensity distribution of the illumination light source 4. Normally, the intensity distribution of a laser is a Gaussian distribution whose center has a higher intensity than the surroundings have. In the Gaussian distribution, since the intensity at its center is extremely intense, it is difficult to form a uniform illuminance distribution on a sample surface. FIG. 4 shows an intensity distribution of light that has passed through the beam shaper 9. By a known method, the bright portion can be equalized so that the Gaussian distribution may be flattened.

For the beam expander 8*a*, a plurality of magnifications can be selected by a switching control system 8'. Needless to say, selection of a plurality of magnifications may be performed by a zoom lens mechanism.

The beam transmitted through the beam shaper 9 is transmitted through a homogenizer 10, then transmitted through a mirror 11 and a converging lens 13, and subsequently irradiated onto a vertical oscillating mirror 14 by a mirror 12. The vertical oscillating mirror 14 is held by a goniometer 16 that is capable of moving in the vertical direction relative to the optical axis. The vertical oscillating mirror 14 is controllable by a control circuit 15. The goniometer 16 is controllable by a control circuit 17. The beam reflected by the vertical oscillating mirror 14 is reflected by a horizontal oscillating mirror 19 by the use of two relay lenses 18. The horizontal oscillating mirror 19 is held by a goniometer 21 that is capable of moving in a horizontal direction relative to the optical axis. The horizontal oscillating mirror 19 is controllable by a control circuit 20. The goniometer 21 is controllable by a control circuit 22.

The beam reflected by the horizontal oscillating mirror 19 is further transmitted through two lenses, a relay lens 23 and an imaging lens 24, bent at a right angle by a polarizing beam splitter (hereinafter referred to as PBS) 25, transmitted through a polarizing element 26, and focused on a pupil 28 of an objective lens 27. That is, the apparatus realizes Koeher's illumination such that the beam from the illumination light source 4 is focused on the pupil 28 of the objective lens 27 by the use of a group of lenses as described above. Here, the installation positions of the vertical oscillating mirror 14 and the horizontal oscillating mirror 19 shall be conjugate to a converging position of the objective lens 27, i.e., the surface of the wafer 1, respectively.

A rotating diffuser plate 29 is used for reducing the coherence produced by the laser. Generally, when the sample is illuminated with coherent light, such as a laser beam, interference fringes having a high coherence called speckle noise are generated, and they appear as a noise on the detected image. Then, it is possible to reduce temporal and spatial coherence by inserting a rotating diffuser plate in the illumination optical path and rotating it. According to an experiment performed by the inventors, it has been found that, by an arrangement in which this rotating diffuser plate 29 is not disposed in a position conjugate to a focal plane of the objective lens 27, but is slightly defocused, the effect can be obtained.

As the objective lens 27, although a refraction type lens is described, a reflection type objective lens may be used. A PBS 25 has an effect such that, if the polarization direction of the illumination light is in parallel to the reflection plane, the PBS 25 reflects it, and if it is perpendicular to the refection plane, the PBS 25 transmits it. Therefore, if a laser beam is used as the illumination light source, since the laser beam is originally a polarized laser beam, it is possible to make the PBS 25 reflect this laser beam totally by matching the direction of polarization.

Moreover, in addition to higher resolution, as described above, because of ultraviolet light is employed, the contrast of the pattern can be enhanced by a polarizing element control circuit 29*a* controlling the polarizing element 26. In order to enhance pattern contrast, paying attention to a fact that the polarization state of the ultraviolet laser beam can be controlled freely by control of the polarizing element 26, the invention makes it possible to control the direction of polarization and the ellipticity of the illumination light and detect a polarizing component that is a part of the detected beam by an image sensor 35. Features of the illumination by the ultraviolet laser beam include a single wavelength and linear polarization. For this reason, by combining the polarizing element 26 provided in an optical path with a ½ wave plate and a ¼ wave plate, its polarization state can be controlled with high efficiency.

Control may be conducted by, for example, rotating the ½ wave plate and the ¼ wave plate around the optical axis. Since pattern contrast varies largely depending on the polarization state of the illumination, which is also dependent on the shape of the sample, the performance of the optical system can be enhanced by making the polarization state controllable (by rotating the wave plate and setting it to an optimal angle). More specifically, it is possible to control the direction of linear polarization by a ½ wave plate of a set of polarizing elements 26 and change its ellipticity by a ¼ wave plate. Thereby, improvement in the detection sensitivity can be achieved. By this combination, parallel Nicols and crossed Nicols can be realized. Naturally, a circularly polarized-light state can be realized as well. Note that these capabilities are not dependent on the illumination wavelength itself.

Note also that as long as the concept is implemented, a configuration to embody the concept may be arbitrary. Needless to say, a spatial filter) not shown in the figure) may be disposed in a position conjugate to the pupil 28 of the objective lens 27 of the optical system that performs bright illumination, thereby attenuating zero-order light (the spatial filter is disposed to block the diffracted light from the pattern, and to lead the scattered light from a foreign material to the image sensor). However, if the polarization is controlled, higher order diffracted light can be extracted more efficiently. According to an experiment by the inventors, it has been found that the contrast is improved by about 20 to 300%.

The beam that was focused into the pupil 28 of the objective lens 27 is irradiated onto the surface of the wafer 1 for illumination. The reflected light therefrom is taken in by the objective lens 27 again, transmitted through the polarizing element 26 and the PBS 25, and is divided into two optical paths by a beam splitter 30. The imaging lens 31 is disposed in such a way that the reflected light is focused to form an image of the pupil 28 of the objective lens 27 on an observation camera 32. This beam splitter 30 sets the quantity of the reflected light to the minimum so that it becomes a minimum necessary light intensity in the observation camera 32. Moreover, an imaging lens 31' is disposed so as to form an image of the wafer 1 on the observation camera 32 by the imaging lens 31'. The imaging lenses 31, 31' can be switched over by a lens switching control circuit 31*a*.

The beam transmitted through this beam splitter 30 is focused into the image sensor 35 by the imaging lens 33*a* and the imaging lens 33*b*. This image sensor 35 has a pixel size of about 0.05 μm to 0.3 μm as converted to a size on the wafer, and outputs a gray-scale image signal according to the brightness (gray level) of the reflected light from the wafer 1. Here, the pixel size is limited, but it can be modified by changing the magnification of the imaging lens 33*b*. For example, for the imaging lens 33*b*, several kinds of imaging lenses with different magnifications are mounted on the apparatus and one of them is selected for a desired magnification by an imaging-lens movement control system 34, whereby a change of magnification can be achieved. Needless to say, for this imaging lens 33*b*, a lens with a zoom mechanism can create the same effect. A pupil filter 41 is disposed at a position conjugate to the pupil 28 of the objective lens 27. It is possible that, for this pupil filter 41, several kinds of pupil filters are mounted on the apparatus and one of them is selected and used by a pupil filter control system 41'.

An output signal of the image sensor 35 is sent to an image processing unit 37 through a driver 36. This driver 36 has a configuration that enables setting of the driving frequency, gain, offset, etc. of the image sensor 35 by external signals. All controls of the image processing unit 37 and other control systems can be performed by a main body control circuit 40.

Figure 5:
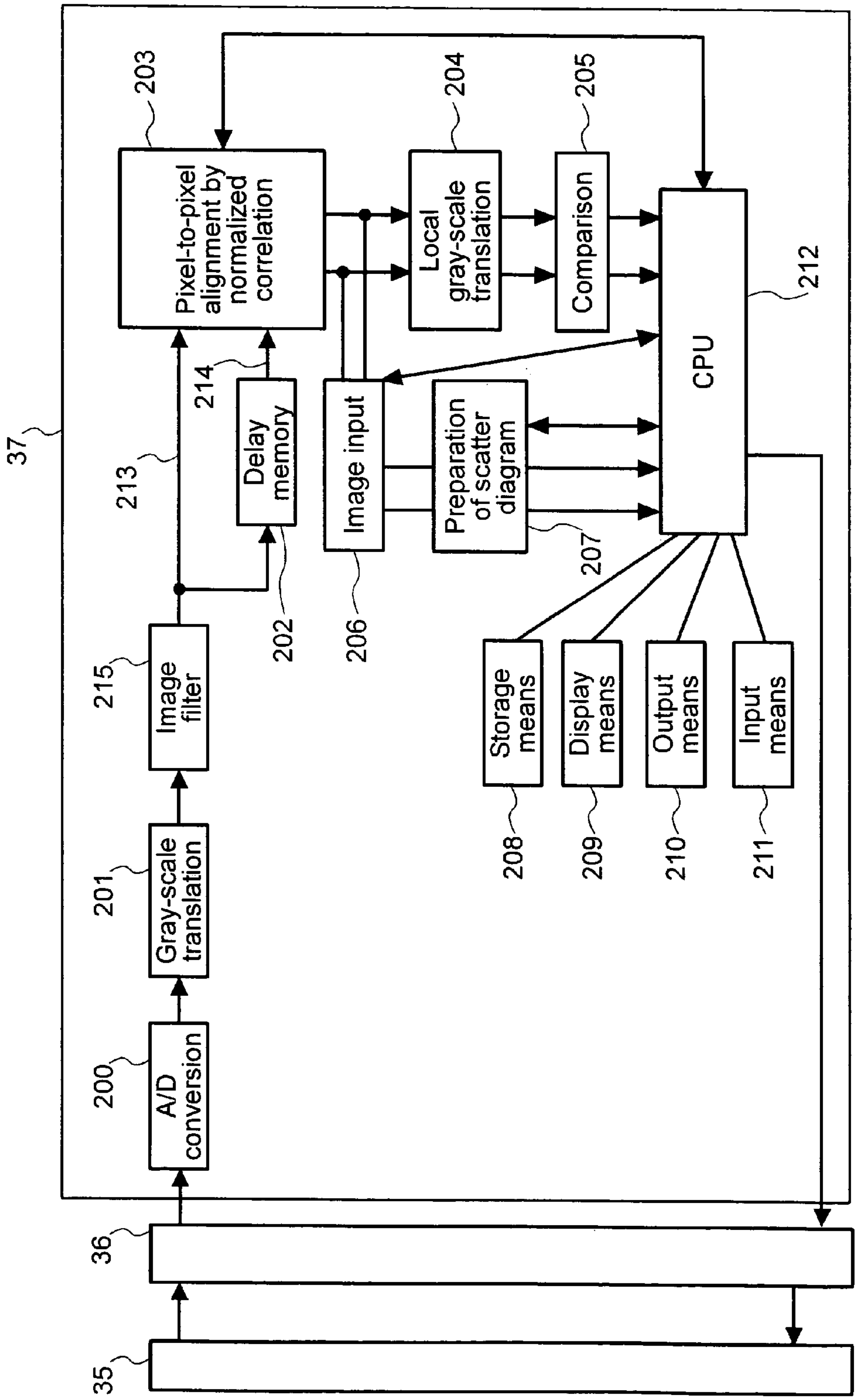
FIG. 5 is a block diagram showing an image processing unit of the apparatus for inspecting an inspection pattern according to this invention.

Next, the image processing unit 37 will be described. FIG. 5 is a diagram showing one example of the image processing unit 37 of the apparatus for inspecting a pattern according to this invention. The image processing unit 37 is composed of an A/D converter 200, a gray-scale translation part 201, an image filter 215, a delay memory 202, an alignment part 203, a local gray-scale translation part 204, a comparison part 205, a CPU 212, an image input part 206, a scatter-diagram preparation part 207, storage means 208, display means 209, output means 210, input means 211, etc.

A gray-scale signal obtained by the image sensor 35 is sent to the image processing unit 37 through the driver 36, and it is converted into a digital image signal by the A/D converter 200, which outputs an image signal of the wafer 1. For example, a 10-bit A/D converter is used. The gray-scale translation part 201 is used for performing such gray-scale translation as disclosed in JP-A No. 320294/1996 to a 10-bit digital image signal outputted from the A/D converter 200. That is, the gray-scale translation part 201 is configured to perform logarithmic transformation, exponential transform, polynomial transform, etc. to correct the image, and to output it, for example, as an 8-bit digital signal.

The image filter 215 is a filter for efficiently rejecting noises peculiar to images detected by ultraviolet light from the image subjected to gray-scale translation. The delay memory 202 is a storage part for memorizing a reference image signal and for memorizing an output image signal from the image filter 215 for a single cell, two or more cells, one chip, or two or more chips that constitute(s) a semiconductor wafer that repeats a cell or a chip in it. Here, the term cell refers to a repeating unit of the pattern in a chip. Incidentally, the image filter 215 may be disposed downstream of the delay memory 202.

The alignment part 203 is a part that detects the amount of positional shift between the image signal (detection image signal obtained from the sample) 213, that was subjected to gray-scale translation and outputted from the gray-scale translation part 201, and a delayed image signal (the reference image signal serving as a reference) 214 obtained from the delay memory 202, by means of normalized correlation, and it performs pixel-to-pixel alignment of the two signals.

The local gray-scale translation part 204 is a part that, for signals that differ from each other in their features (brightness, derivative value, standard deviation, texture, etc.), performs gray-scale translation on both or one of the image signals so that the features may become equal to each other. The comparison part 205 is a part that detects a defect based on a difference in a feature by comparing detection image signals that were subjected to gray-scale translation in the local gray-scale translation part 204. That is, the comparison part 205 compares the reference image signal, that was delayed by an amount corresponding to a cell pitch etc. and was outputted from the delay memory 202, and the detected detection image signal.

Coordinates of array data etc. on the wafer 1 are inputted in advance through the input means 211 consisting of a key board, a disk, etc. The CPU 212 creates defect inspection data based on the coordinates of the array data etc. on the wafer 1 and stores it in the storage means 208. This defect inspection data can be displayed on the display means 209, such as a display, if needed, and can be outputted to the output means 210. Here, the comparison part 205 can be one that is disclosed in JT-A 212708/1986. For example, it consists of an image alignment circuit, a difference image detection circuit for images that were aligned mutually, a mismatch detection circuit for digitizing a difference image, and a feature extraction circuit for calculating area, length (projected length), coordinates, etc. from a binarized output.

The image input part 206 inputs an image in order to prepare a scatter diagram of two images that were aligned pixel-to-pixel in the alignment part 203. The scatter-diagram preparation part 207 is used for preparing a scatter diagram between the feature of the detected image and the feature of a reference image on a category basis for the images inputted into the image input part 206 and for displaying it in, for example, the display means 209.

Figure 6:
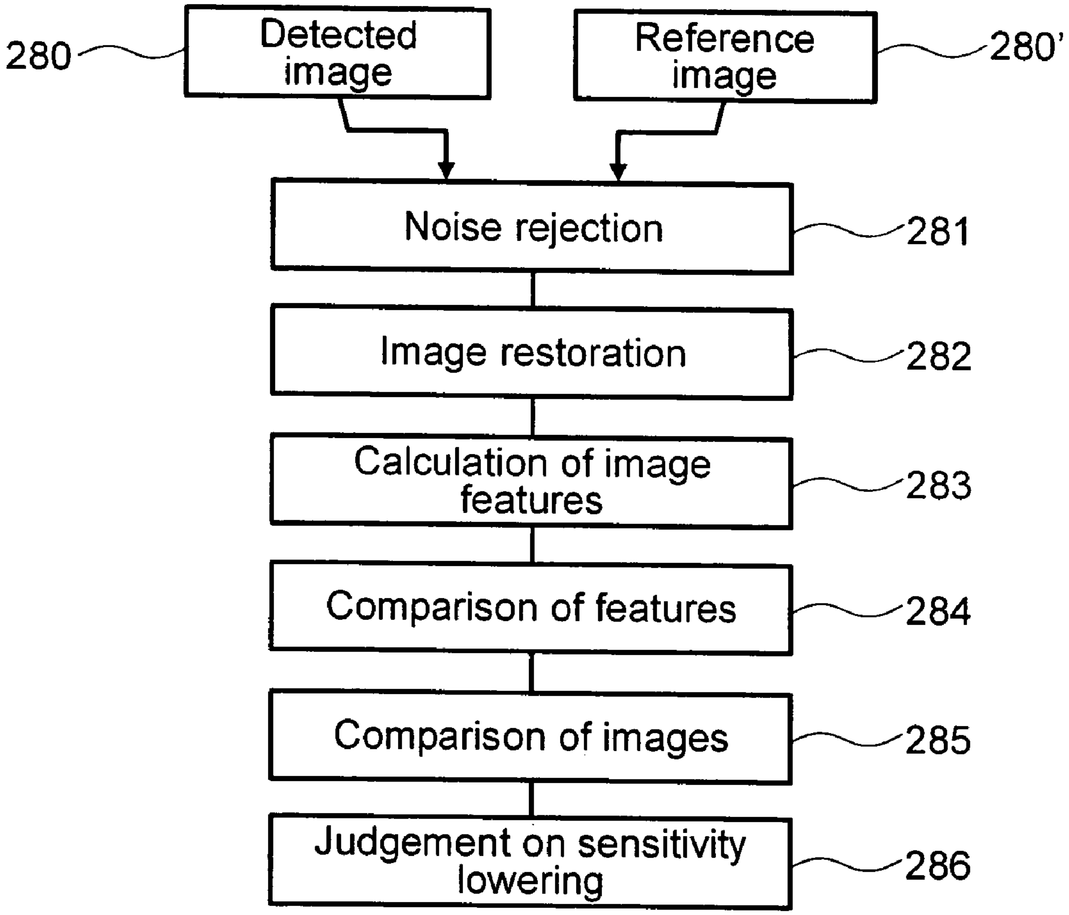
FIG. 6 is a flow diagram illustrating the flow of image processing according to this invention.

FIG. 6 shows one example of the flow of image processing in the apparatus for inspecting a pattern according to this invention. One example of the image filter 215 will be described. First, an inputted detected image 280 and a reference image 280' are, if necessary, subjected to noise rejection (Step 281) and improvement of image quality to improve the S/N. For noise rejection, various filters are provided and can be selected according to an object and the quality of noise. One example of such filters is a filter used for a method using values of surrounding pixels with a weight added. More specifically, the filter adds values of pixels (n×m) surrounding a target pixel, after values were multiplied by filter coefficients.

Figure 7:
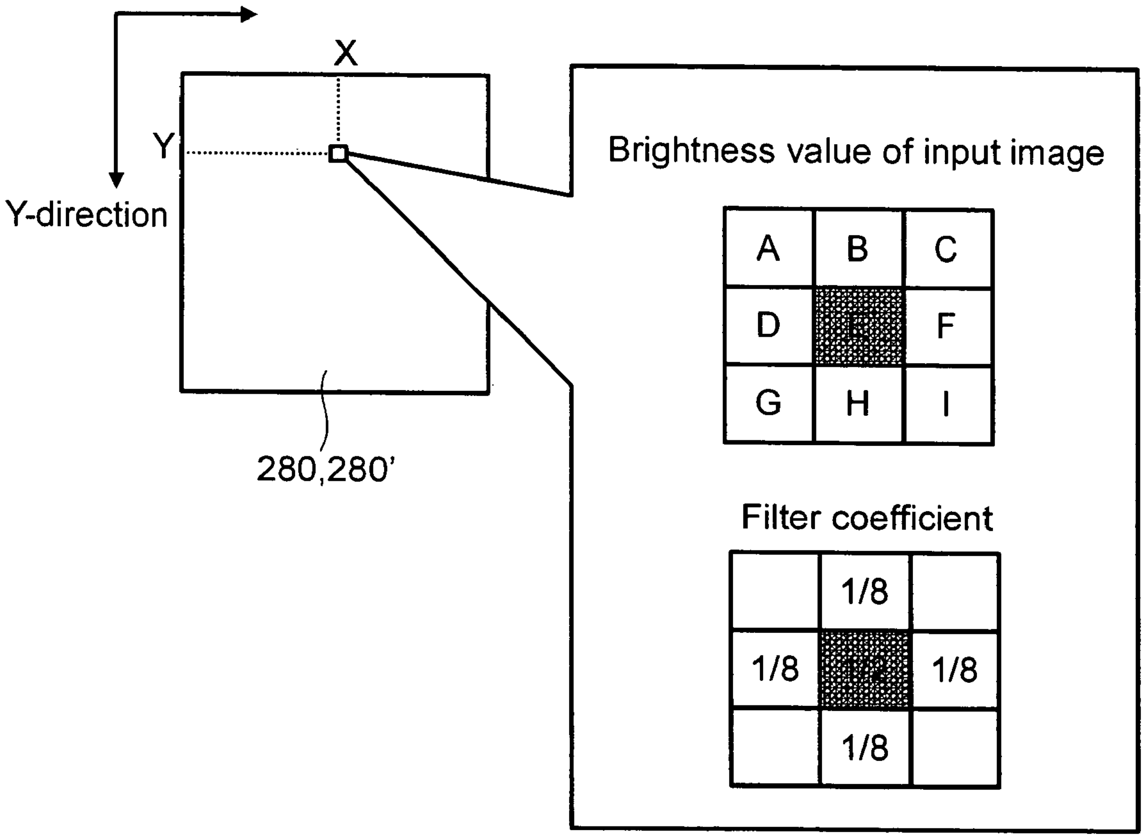
FIG. 7 is a diagram illustrating the image filter for image processing according to this invention.

FIG. 7 shows one example of filtering in image processing carried out by the apparatus for inspecting a pattern according to this invention. FIG. 7 shows a case where m and n are set to m=n=3 and the weight of neighboring pixel values is ⅛. A value of a target pixel is expressed by the following formula 1.

$$F(i,j)=B\cdot\tfrac{1}{8}+D\cdot\tfrac{1}{8}+F\cdot 1/8+H\cdot\tfrac{1}{8}+E\cdot\tfrac{1}{2} \quad (1)$$

The size and coefficient of a filter can be changed flexibly using a look-up table. As another example, there is a median filter. This filter takes the median of brightness values in the neighborhood, and it can remove the influence of a singular point. Moreover, another example uses a Gaussian function.

$$G(x,y)=(\tfrac{1}{2}\pi\sigma^2)\cdot\exp(-(x^2+y^2)/2\sigma^2) \quad (2)$$

$$F(x,y) = G(x,y)\otimes f(x,y) \quad (3)$$

$$= \int\int G(x+u, y+v)\cdot f(x,y)\,du\,dv$$

(但し，⊗はたたみ込み)

This is done in such a way that an image f (x, y) is convoluted as specified by formula 3 with a two-dimensional Gaussian function (formula 2) of a mean of 0 and divergence of $\sigma^2$, thereby smoothing the image. Moreover, in another example, noises occurring regularly can be rejected by using Fourier conversion.

Next, an image that is deteriorated by rejection of noises is restored (Step 282). As one example, the restoration of an image is performed with the use of a Wiener filter. This restoration provides an image in which a mean squared error between the input image f (x, y) and a restored image f' (x, y) becomes the minimum.

Further, the image is checked to determine whether or not there exists a large difference in visual performance between the detected image and the reference image that are to be compared. Evaluation indices include contrast, variation (standard deviation) in brightness, frequencies of noise components, etc. If there is a large difference in these features between the images, these features are calculated (Step 283), subsequently the calculated features are compared (Step 284), and a combination of images is produced (Step 285). Moreover, if the image is in a level such that a combination of features cannot be obtained in the detection process, the sensitivity is lowered in the comparison part so that false information is prevented from occurring. After the judgement on sensitivity lowering (Step 286) is performed, its result is displayed in the display means 209 etc. Incidentally, a detailed method of calculating defects in the image processing unit 37 is feasible by use of a method disclosed in JP-A No. 194323/2001 etc.

Figure 8:
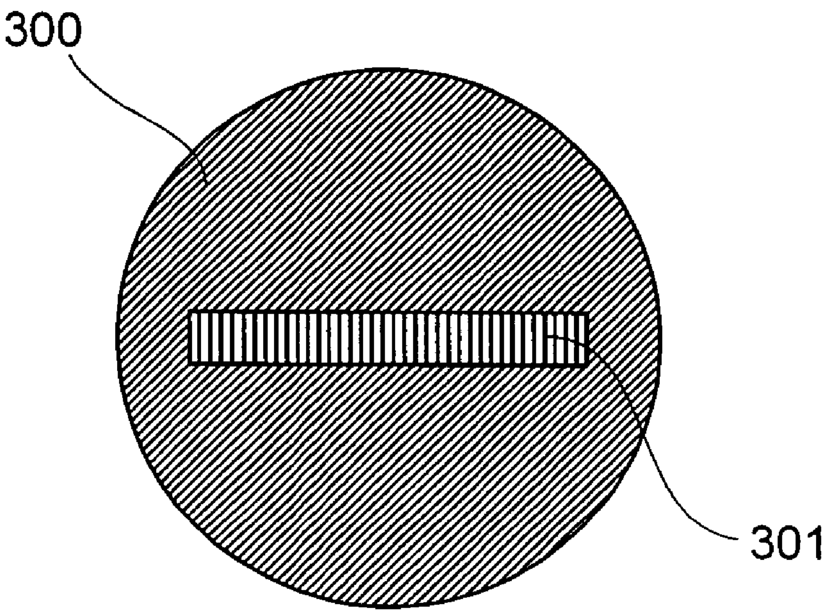
FIG. 8 is a diagram showing a relationship between a detection range of the image sensor on the visual field according to this invention and an illumination region.
Figure 9:
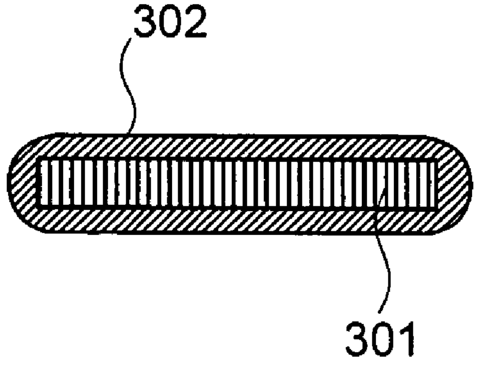
FIG. 9 is a diagram showing a relationship between the detection range of the image sensor on the visual field according to this invention and the illumination region.

Next, the shape of illumination that is irradiated onto the wafer 1 will be described. In the case where a one-dimensional sensor is used as an image sensor, as shown in FIG. 8, even when the whole plane of the visual field 300 is illuminated, illumination that contributes to detection is only a region 301, and the remaining area that occupies a major portion of the optical power will not contribute to detection. In the light of this situation, in order to improve the illuminance, it will be favorable to perform linear illumination, like an area 302, to the one-dimensional sensor, as shown in FIG. 9. In accordance with this invention, the image sensor is constructed by using a time-delay and integration type sensor, that is, a TDI (Time Delay &Integration) type sensor among CCD sensors. In the TDI sensor, N-steps (a few tens of steps to 256 steps or so, or in some case 10000 steps) of light receiving parts each called a stage are arranged in a short-side direction, and a plurality of these stages are aligned in a long-side direction to form a one-dimensional sensor.

Figure 10:
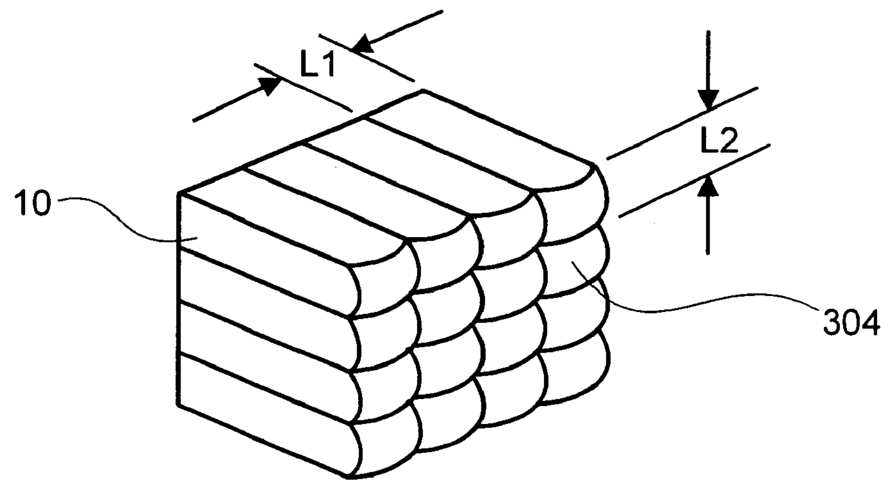
FIG. 10 is a diagram illustrating a homogenizer for illumination according to this invention.

An example of implementing this rectangular illumination will be described with reference to FIG. 10. For the homogenizer 10, a plurality of lens array elements 304 are used, each arranged to form a rectangular shape. Since the difference between the long side L1 and the short side L2 results in the difference in a range to be illuminated, the illumination of a rectangular shape is possible. In the case of L1=L2, it becomes a circular illumination. Moreover, since a plurality of the lens array elements 304 are arranged, a plurality of point light sources can be realized on the pupil. These point light sources are imaged on the pupil 28 of the objective lens 27, and, consequently, it is possible to suppress nonuniformity of illumination to the sample in cooperation with the beam shaper 9.

Figure 11:
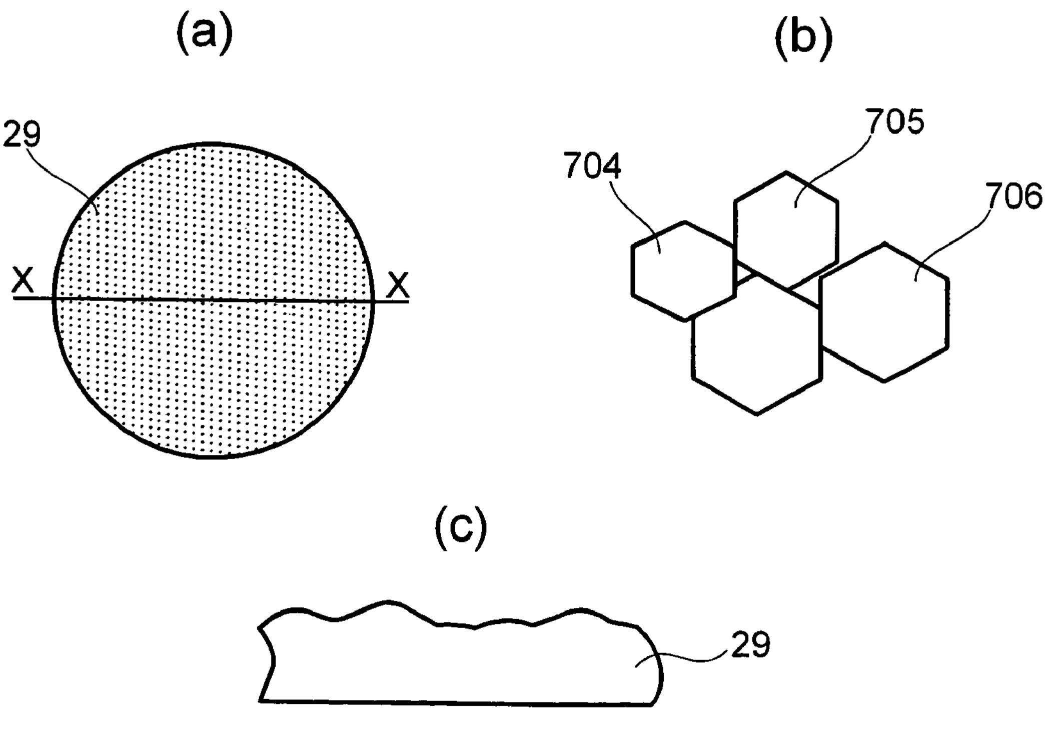
FIG. 11(*a*) to FIG. 11(*c*) are diagrams illustrating the shape of a rotating diffuser plate according to this invention, wherein FIG. 11(*a*) is a front view, FIG. 11(*b*) is a detail view of a diffusing surface and FIG. 11(*c*) is a cross-sectional view taken alone line X-X in FIG. 11(*a*).

Next, the rotating diffuser plate will be described. FIGS. 11(*a*), 11(*b*) and 11(*c*) show an example of the shape of the rotating diffuser plate 29. FIG. 11(*a*) is a front view and FIG. 11(*b*) is a detail view of a diffusing surface. FIG. 11(*c*) shows a cross section along line X-X in FIG. 11(*a*). Preferably, the rotating diffuser plate 29 is formed by randomly arranging grains 704, 705, 706 whose shape is a polygonal or circular form with a diameter of about 0.1 mm, as seen from the surface. Moreover, it is desirable that nonuniformity in the cross section is random both in size and in shape according to the grain size. Temporal and spatial coherence of light can be reduced by rotating this rotating diffuser plate 29 at high speed within a storage time of the image sensor 35, and, thereby, the optical coherence can be removed.

As a method for rotating it at high speed, the use of an air-turbine motor makes it possible to realize a rotational frequency of a few kHz. However, if the intention is to realize a rotational frequency of a few kHz, eccentricity between the rotating diffuser plate 29 and the motor may occur depending on their fixing state, resulting in vibration when being rotated, and, in the worst case, it may affect the precision of the apparatus itself. As a result, the inventors propose a method of realizing low temporal and spatial coherence of light at such a low speed that the rotational frequency of the rotating diffuser plate 29 does not reach the storage time of the image sensor 35.

Figure 12:
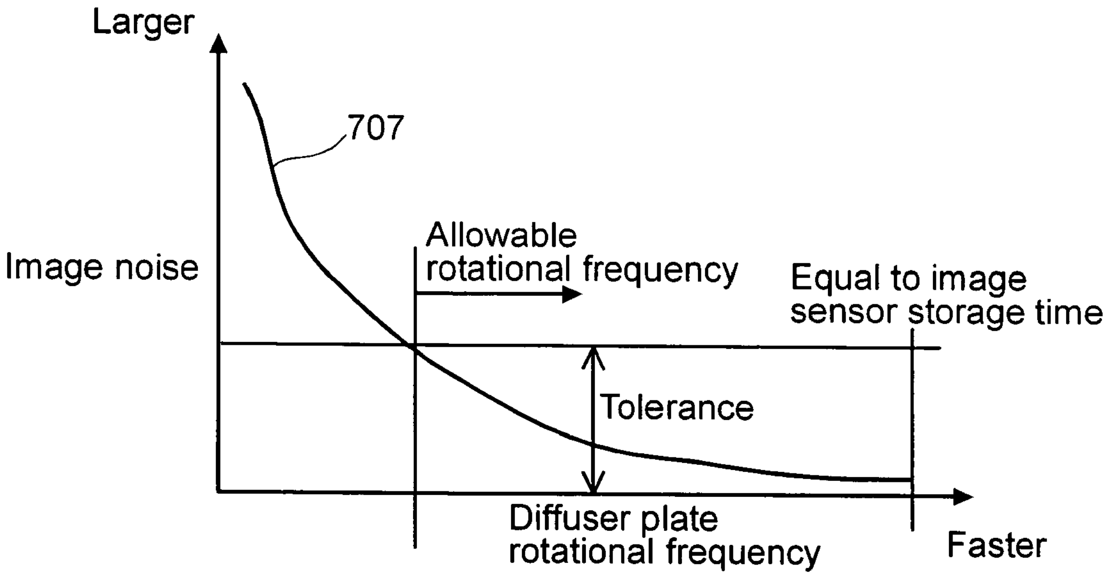
FIG. 12 is a graph illustrating rotational frequency and coherence of the rotating diffuser plate according to this invention.

FIG. 12 shows a relationship between image noise and the rotational frequency of the rotating diffuser plate. The horizontal axis represents the rotational frequency of the rotating diffuser plate, the right direction corresponding to faster rotation. The vertical axis represents image noise, the upward direction corresponding to larger noise. The image noise stands for the coherence on the sample. The image was taken in actually by the image sensor 35. The waveform 707 is a random noise measured at that time. When the coherence is large, the image noise will become large; when it is small, the case corresponds to sufficiently reduced coherence. The figure indicates that, as the rotational frequency of the rotating diffuser plate is set to be faster, the image noise becomes smaller. Since the image noise is only required to be equal to or less than the noise at defect judgement, the rotational frequency may be set to any value within a tolerance. This rotational frequency is approximately one quarter of the storage time of the image sensor.

Figure 13:
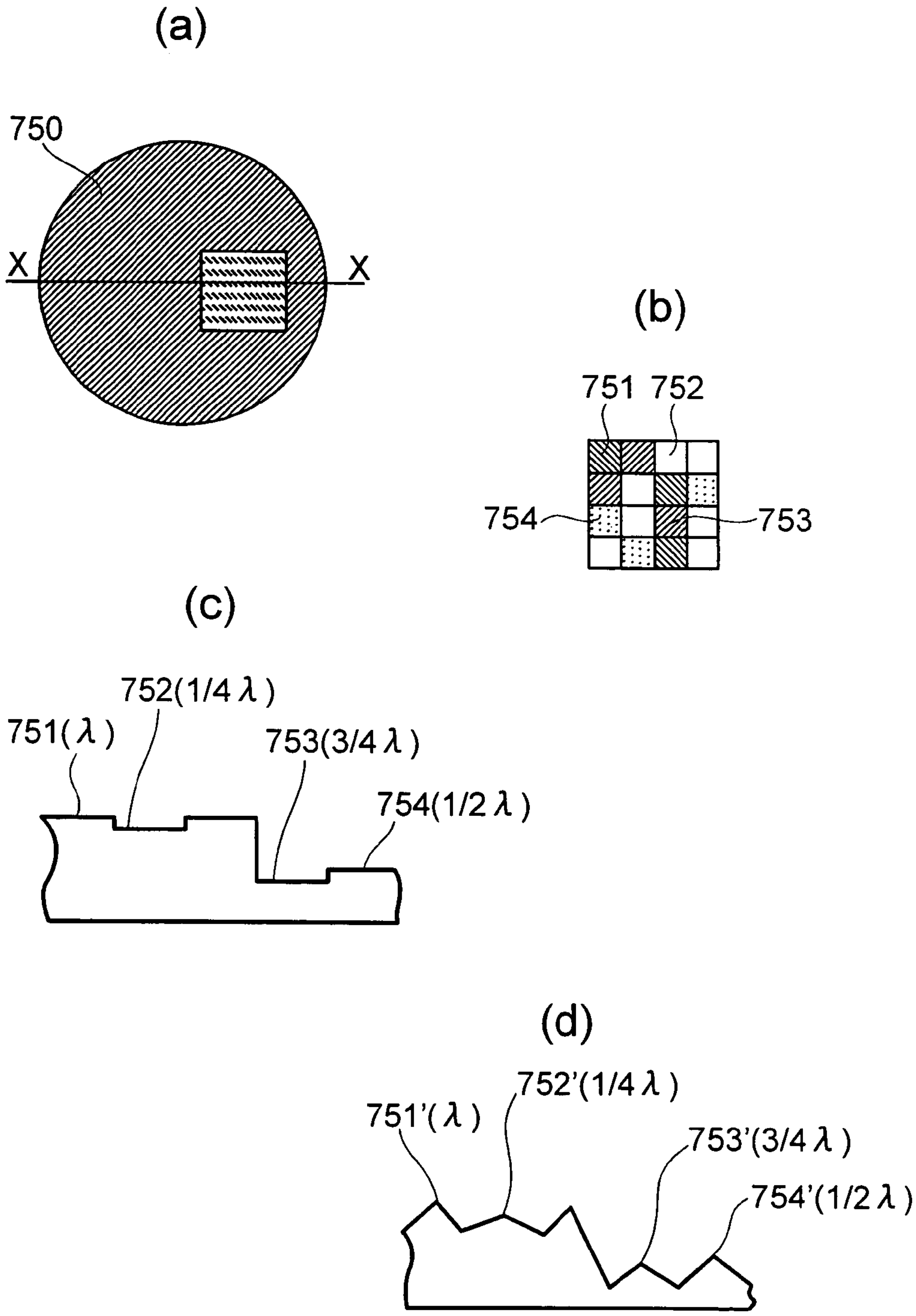
FIG. 13(*a*) to FIG. 13(*d*) are diagrams illustrating a random phase plate according to this invention, wherein FIG. 13(*a*) is a front view, FIG. 13(*b*) is a detailed view of the plate surface, and FIG. 13(*c*) are cross-sectional views taken along line X-X in FIG. 13(*a*).

Moreover, even if a rotating phase plate is installed at the position of the rotating diffuser plate 29, the same effect can be obtained. FIGS. 13(*a*) to 13(*d*) are directed to features of a rotating phase plate 750. FIG. 13(*a*) is a front view, FIG. 13(*b*) is a view showing details, and FIG. 13(*c*) is a view showing a cross section along line X-X in FIG. 13(*a*). At a location 751, the rotating phase plate 750 is specified to have a thickness that does not change the phase. The rotating phase plate 750 is formed so that the steps are set as follows: a step 754 equal to a phase difference of ½λ; a step 752 equal to a phase difference of ¼λ; a step 753 equal to a phase difference of ¾λ; and the like. A large number of differences in level having different depths are formed at random. By fixing this rotating phase plate to the motor instead of the rotating diffuser plate 29 and rotating it, the coherence of the laser beam can be reduced, because the phase of the laser beam passing through each step can be varied according to the depth of the each step.

Moreover, FIG. 13(*d*) shows an example in which the upper surface of the step is made up of projections rather than a flat surface. More specifically, the upper surfaces of the protrusions are formed in such a way that: at a location 751', the protrusion has a height that does not change the phase; at a step 754', there is a phase difference of ½λ is introduced; at a step 752', there is a phase difference of ¼λ; at a step 753', a phase difference of ¾λ; etc. Since the phase of the laser beam can be varied according to the depth of each step similarly, the coherence of the laser beam can be reduced. In addition, the protrusions have different angles, which causes an effect of spreading out the beam; therefore, the coherence can be further reduced.

Figure 14:
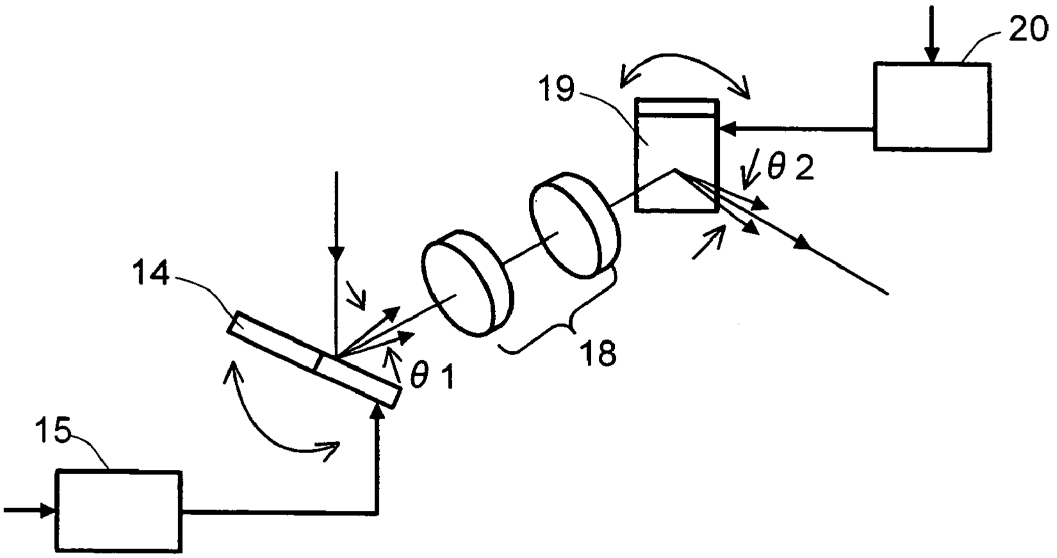
FIG. 14 is a diagram illustrating an arrangement of oscillating mirrors according to this invention.

Next, the oscillating mirrors will be described. FIG. 14 is a view showing an arrangement of the oscillating mirrors. One of the mirrors is arranged so as to be rockable in the vertical direction, and the other is arranged so as to be rockable in the horizontal direction. The vertical oscillating mirror 14 can oscillate vertically by only an oscillating angle θ1 relative to the center of the optical axis by the control circuit 15. The horizontal oscillating mirror 19 can oscillate horizontally by only an oscillating angle θ2 relative to the center of the optical axis by the control circuit 20. The oscillating mirrors 14 and 19 are placed substantially in the same conjugate positions by the use of a relay lens 18.

Figure 15:
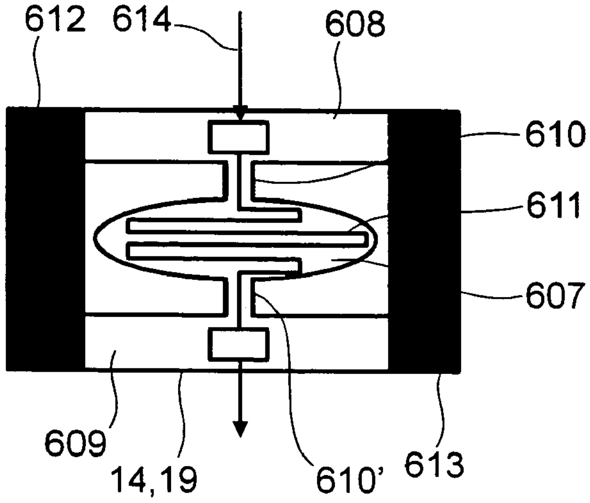
FIG. 15 is a diagram illustrating the structure of the oscillating mirror according to this invention.

FIG. 15 illustrates an example of the structure of the oscillating mirrors. Each of the oscillating mirrors 14, 19 is manufactured in such a way that a part for fixing and a part for oscillating are integrated into one body. That is, bars 610, 610' that protrude from fixing sides 608, 609 hold a rockable plane member 607. A coil 611 is formed on the plane member 607. Magnets 612,613 are provided on the both ends of the coil 611. The above-described members constitute a structure in which, by causing a current 614 to flow in the coil 611, the coil 611 repels the magnets 612,613, and, consequently, the plane member 607 oscillates. Incidentally, on the backside of the plane member 607, a coating for totally reflecting the laser beam is processed, thus serving as a mirror. It was confirmed that if a fixed current is flows, the plane member 607 oscillates at a constant frequency.

Figure 16:
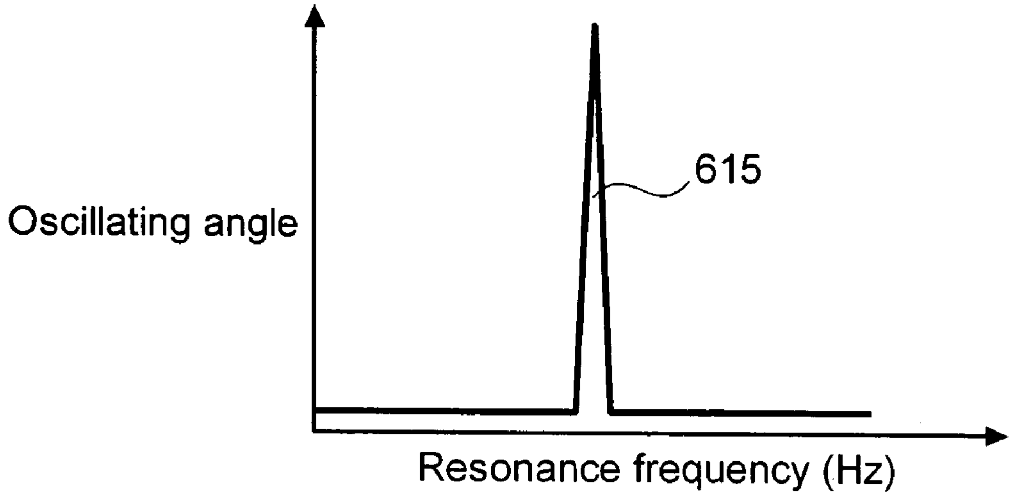
FIG. 16 is a graph illustrating a frequency characteristic of the oscillating mirror according to this invention.

FIG. 16 shows a frequency characteristic. The horizontal axis represents the resonance frequency, and the vertical axis represents the oscillating angle. The peak resonance frequency may be set to an arbitrary frequency in a range from 1000 Hz to 5000 Hz. Controlling this frequency is feasible by changing the width of the bars 610, 610'. Needless to say, a frequency less than 1000 Hz is also possible. The oscillating mirrors are manufactured in such a way that the oscillating angle becomes the maximum at a predetermined frequency. In order to make the oscillating mirrors oscillate with the same phase in both the vertical direction and the horizontal direction, it is desirable to use oscillating mirrors having the same resonance frequency.

Figure 17:
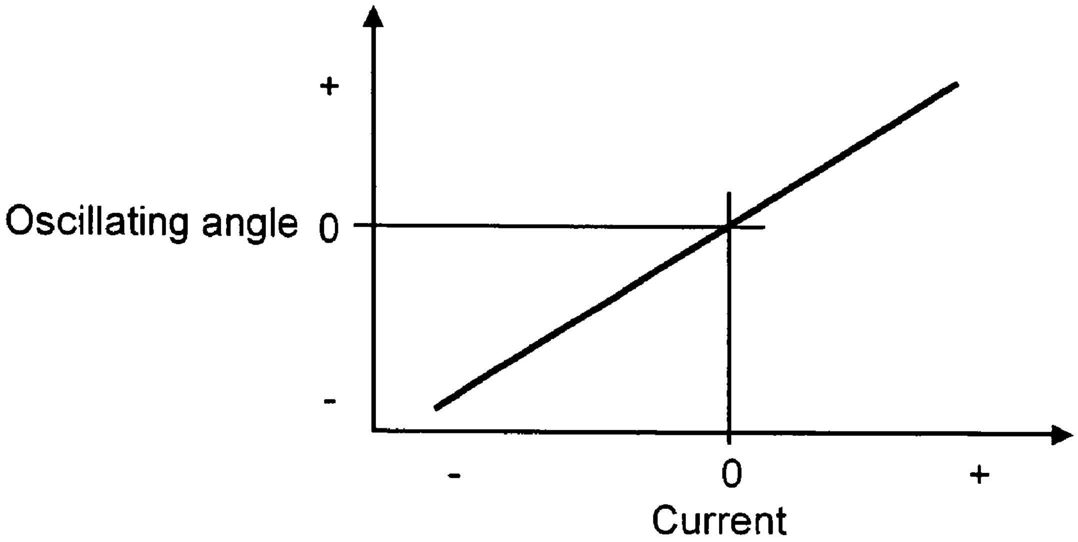
FIG. 17 is a graph illustrating a relationship of the oscillating angle and the current value of the oscillating mirror according to this invention.

FIG. 17 shows a relationship between current value and oscillating angle with the current set forth along the horizontal axis and the oscillating angle indicated on the vertical axis. When no current is fed, resonance does not occur because no current passes through the coil. Therefore, the mirror stands still in a neutral position. Feeding a current alternately in positive and negative directions makes the mirror oscillate at a resonance frequency. This oscillating angle can be arbitrarily set up by controlling the current. Furthermore, it is desirable that the resonance frequency of the oscillating mirror is synchronized with the storage time of the image sensors 35. For example, in the case where the driving frequency is set to 300 kHz and the number of stages is chosen to be 500, an image will be acquired at 600 Hz. If the resonance-type oscillating mirror that oscillates is designed to have a frequency of 600 kHz, one revolution of oscillation within the storage time is feasible. Further, if the frequency of the resonance-type oscillating mirror goes to, for example, 611 Hz etc., which is different from an ideal frequency due to variation at the time of manufacture, alteration of the driving frequency of the image sensor to 305.5 kHz will realize one revolution of oscillation within the storage time. That is, an ideal oscillating and image acquisition will become possible by matching one of the image acquisition time by the image sensor and the frequency of the resonance-type oscillating mirror to the other thereof.

Next, a method of oscillating the mirror will be described. The oscillating mirrors 14, 19 allow for independent control, respectively. Here, the control refers to the oscillating angle.

Figure 18:
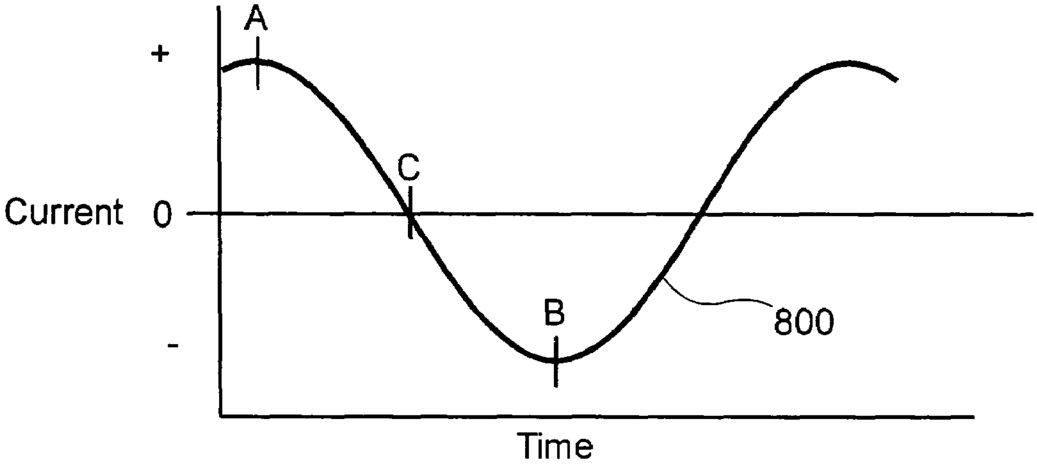
FIG. 18 is a diagram illustrating an example of an operation of the oscillating mirror according to this invention.
Figure 19:
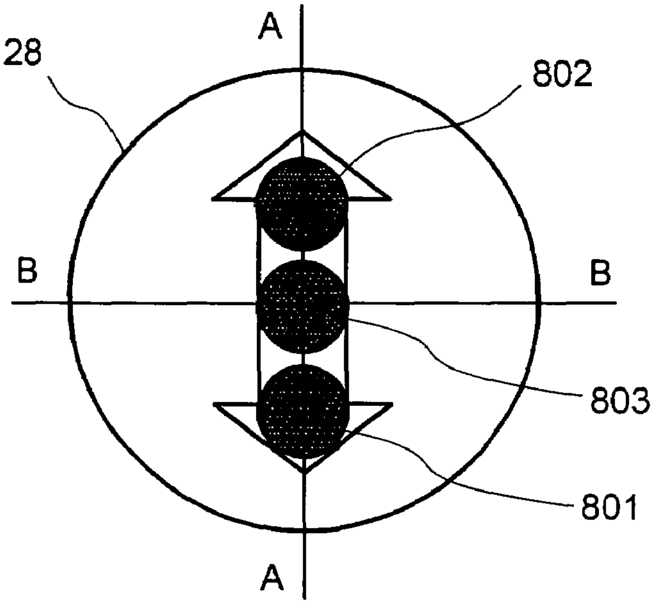
FIG. 19 is a diagram showing a situation where an operation of the oscillating mirror according to this invention on the pupil is observed.
Figure 20:
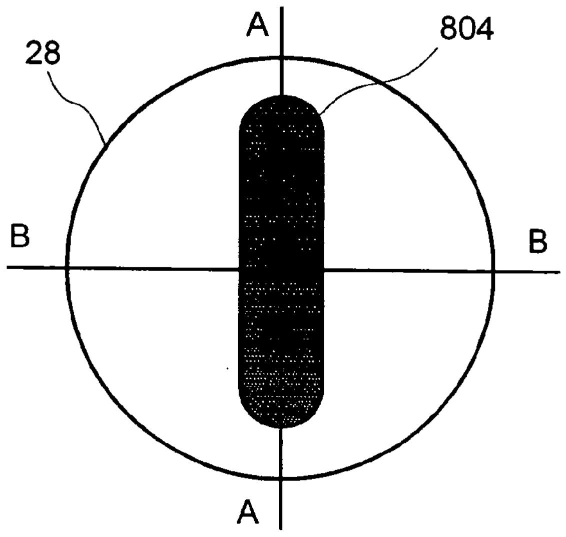
FIG. 20 is a diagram showing a situation where an operation of the oscillating mirror according to this invention on the pupil is observed.
Figure 21:
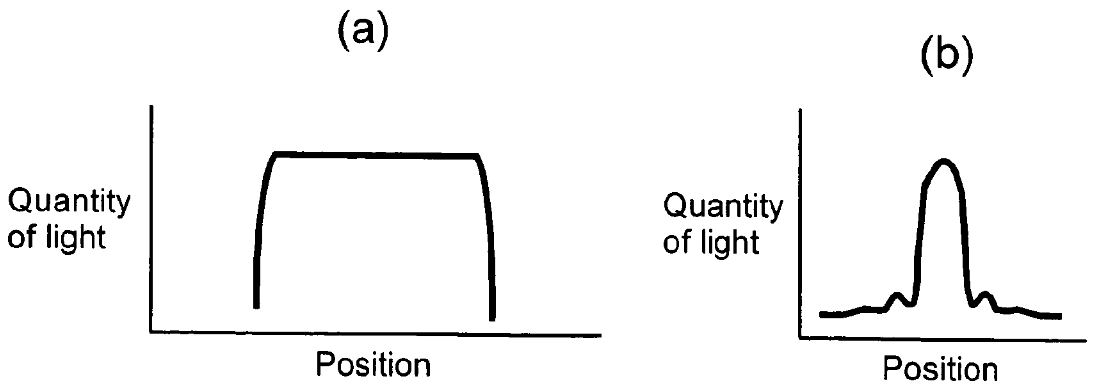
FIG. 21(*a*) and FIG. 21(*b*) are diagrams illustrating an illuminance distribution on the pupil resulting from an operation of the oscillating mirror according to this invention, wherein FIG. 21(*a*) shows the distribution along line A-A in FIG. 20, and FIG. 21(*b*) shows the distribution along line B-B in FIG. 20.

First, a state where the vertical oscillating mirror 14 is driven and the horizontal oscillating mirror 19 is frozen will be described. FIG. 18 shows an example of the controlled movement of the vertical oscillating mirror 14. The horizontal axis represents time and the vertical axis represents current. As mentioned above, the variation in the current causes a change in the oscillating angle. The curve 800 is a pattern of the current fed to the vertical oscillating mirror 14. FIG. 19 shows an image obtained by the observation camera 32 on the pupil 28 when the wafer 1 is set. The wafer 1 is assumed to be a polished wafer. At time A in FIG. 18, a spot of the illumination is located in the lowermost position 801 in the pupil 28. At time B, the spot is located in the uppermost position 802 similarly. At time C, the spot will be located in the center 803 of the pupil when the current is zero. FIG. 20 shows an image taken by the observation camera 32 when the osculating mirror is driven for one cycle. It is assumed that the picture-taking cycle of the observation camera is made equal to the driving cycle of the image sensor. One cycle of driving yields a spot shape 804. FIGS. 21(*a*) and 21(*b*) show the light intensity distribution of this spot 804 on the pupil 28 by the observation camera. FIG. 21(*a*) shows the light intensity distribution of a cross section A-A in FIG. 26, and FIG. 21(*b*) shows the light intensity distribution of a cross section B-B in FIG. 20. A uniform illuminance distribution, which is obtained in a range of movement in the oscillating direction, can be obtained. An illuminance distribution is also obtained in a direction in which it does not move.

Figure 22:
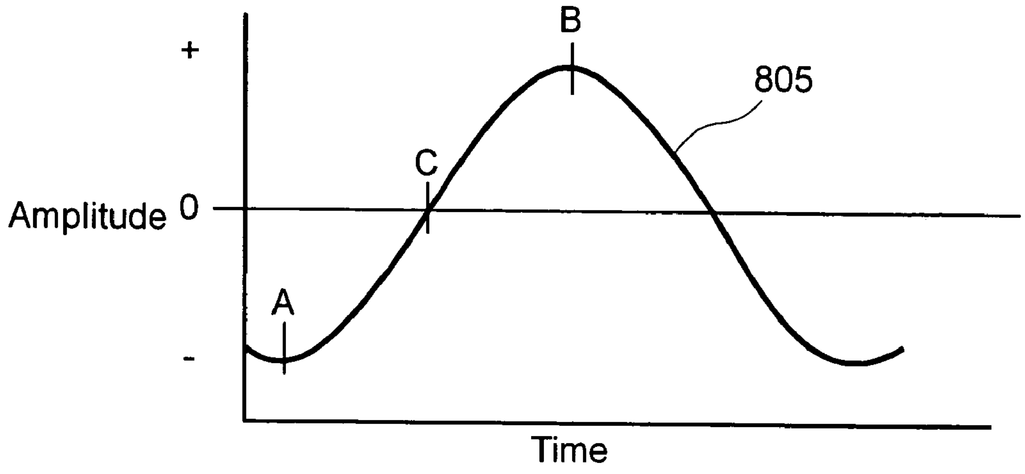
FIG. 22 is a diagram illustrating another example of an operation of the oscillating mirror according to this invention.
Figure 23:
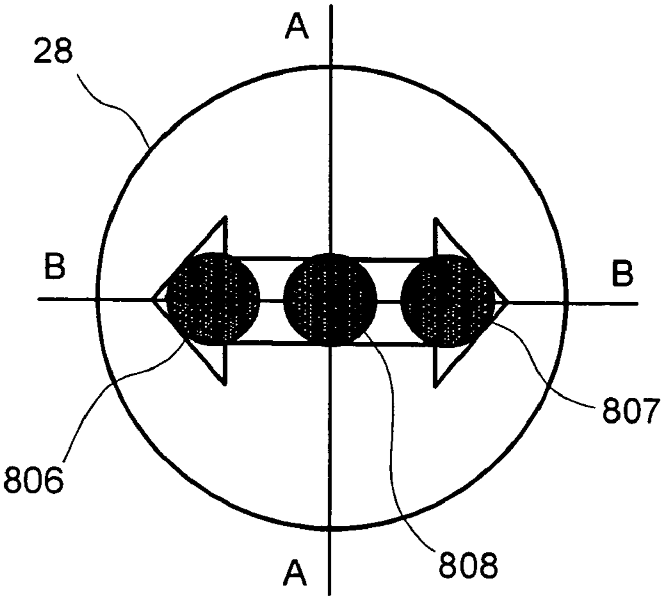
FIG. 23 is a diagram showing a situation where an operation of the oscillating mirror according to this invention on the pupil is observed.
Figure 24:
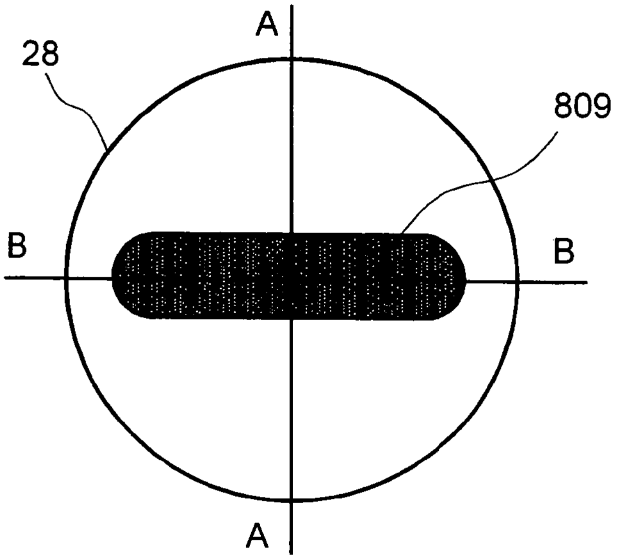
FIG. 24 is a diagram showing a situation where an operation of the oscillating mirror according to this invention on the pupil is observed.
Figure 25:
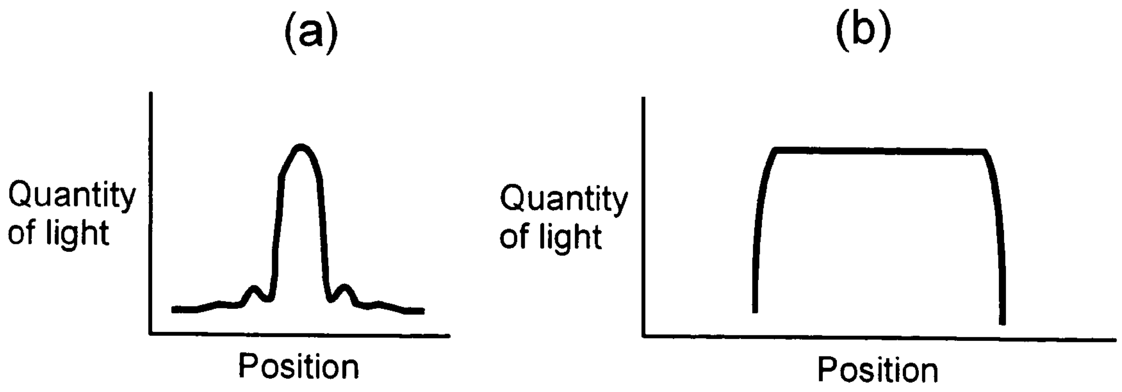
FIG. 25(*a*) and FIG. 25(*b*) are graphs illustrating an illuminance distribution on the pupil resulting from an operation of the oscillating mirror according to this invention, wherein FIG. 25(*a*) shows the distribution along line A-A in FIG. 24, and FIG. 25(*b*) shows the distribution along line B-B in FIG. 24.

Next, a state where the horizontal oscillating mirror 19 is driven and the vertical oscillating mirror 14 is made to stand still will be described. FIG. 22 shows an example in which the horizontal oscillating mirror 19 is controlled. The horizontal axis represents time and the vertical axis represents current. A pattern of the current 805 is given to the horizontal oscillating mirror 19. FIG. 23 shows an image of the pupil 28 taken by the observation camera 32. At time A in FIG. 23, the spot of illumination is located in the leftmost position 806 in the pupil 28. At time B, the spot is located in the rightmost position 807 in the pupil 28. At time C, that is when the current is zero, the spot will be located in the center 808 of the pupil 28. FIG. 24 shows an image taken by the observation camera 32 when it is driven for one cycle. One cycle of driving the mirror provides an illumination spot having a shape 809. FIGS. 25(*a*) and 25(*b*) show the light intensity distribution of this spot 809 on the pupil 28 by the observation camera. FIG. 25(*a*) shows the light intensity distribution along the cross section A-A in FIG. 24, and FIG. 25(*b*) shows the light intensity distribution along the cross section B-B in FIG. 24. A uniform illuminance distribution can be obtained in a range in which the mirror moves in the oscillating direction. An illuminance distribution that depends on the spot will be obtained in a direction of no oscillation. That is, the illuminance distribution will be obtained in a direction 90 degrees rotated from the direction of the spot when the vertical oscillating mirror 14 is oscillated.

Figure 26:
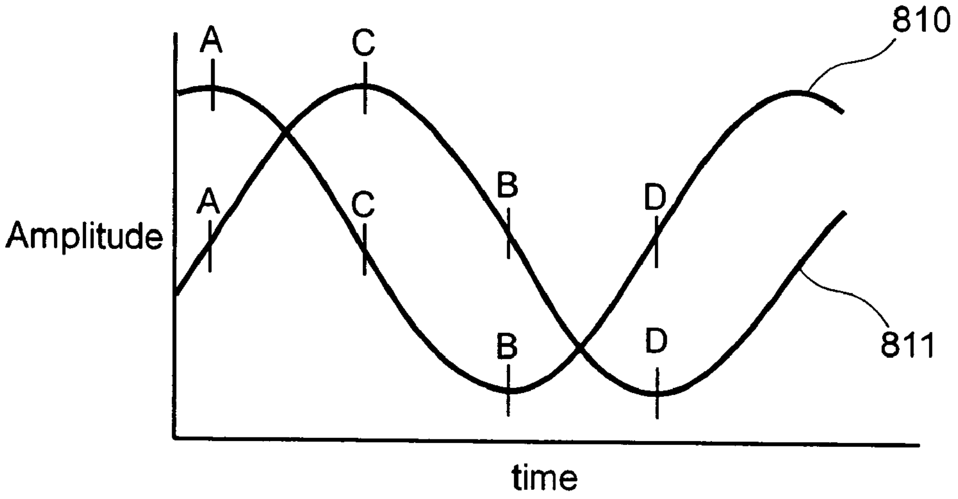
FIG. 26 is a timing diagram illustrating another example of an operation of the oscillating mirror according to this invention.
Figure 27:
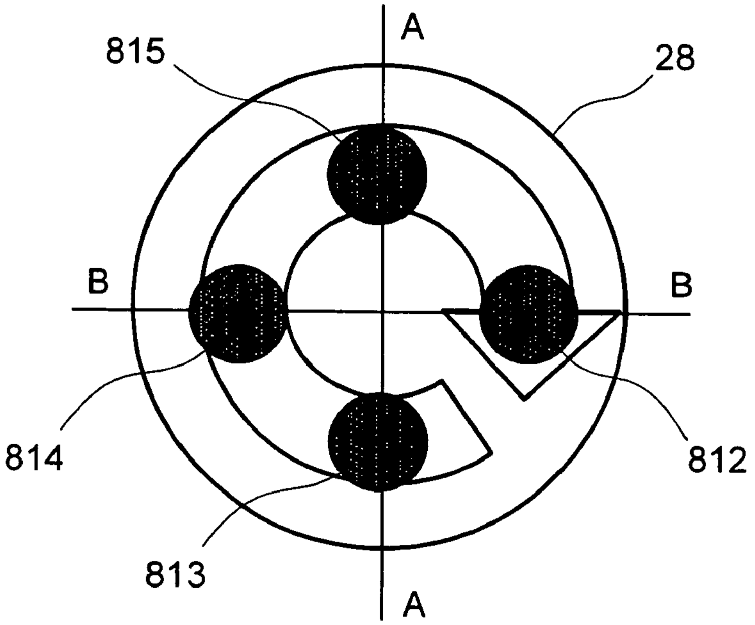
FIG. 27 is a diagram showing a situation where an operation of the oscillating mirror according to this invention on the pupil is observed.
Figure 28:
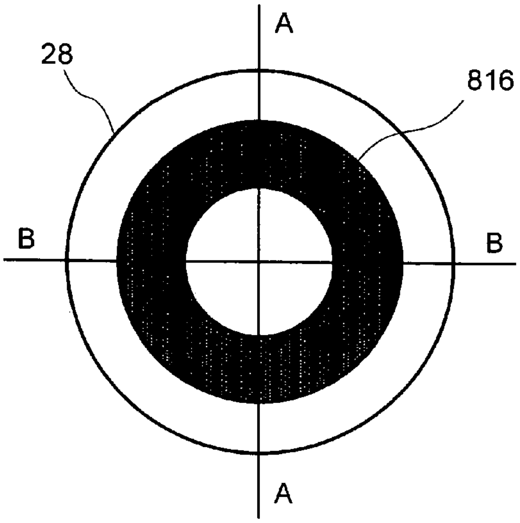
FIG. 28 is a diagram showing a situation where an operation of the oscillating mirror according to this invention on the pupil is observed.
Figure 29:
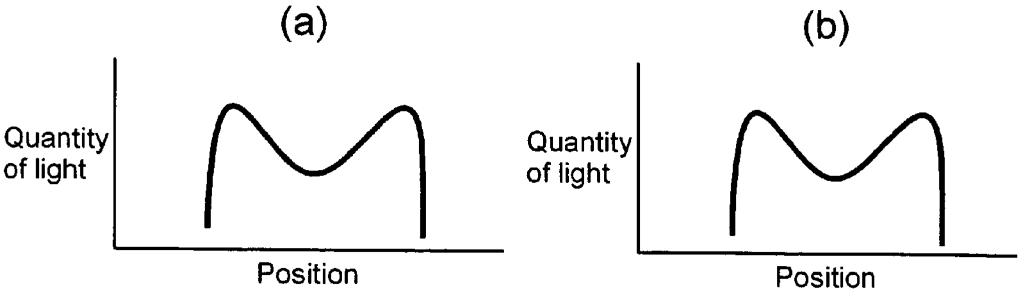
FIG. 29(*a*) and FIG. 29(*b*) are graphs illustrating an illuminance distribution on the pupil resulting from an operation of the oscillating mirror according to this invention, wherein FIG. 29(*a*) shows the distribution along line A-A in FIG. 28, and FIG. 29(*b*) shows the distribution along line B-B in FIG. 28.

Next, a state in which both oscillating mirrors are driven simultaneously will be described. FIG. 26 shows an example in which both oscillating mirrors are controlled. The horizontal axis represents time and the vertical axis represents current. A pattern 810 of movement is given to the horizontal oscillating mirror 19, and a pattern 811 of movement is given to the vertical oscillating mirror 14. FIG. 27 shows an image of the pupil 28 taken by the observation camera 32. The spot of illumination is located in the following positions: in the rightmost position 812 in the pupil at time A in FIG. 26; in the lowermost position 813 at time B; in the leftmost position 814 at time C; and in the uppermost position 815 at time D; the spot coming back to its original position after one cycle. FIG. 28 shows an image taken by the observation camera 32 when the mirrors are driven for one cycle. The image takes the shape of a spot 816. FIGS. 29(*a*) and 29(*b*) show the light intensity distribution of this spot 816 on the pupil 28 taken by the observation camera. FIG. 29(*a*) shows the light intensity distribution along the cross section A-A in FIG. 28, and FIG. 29(*b*) shows the light intensity distribution along the cross section B-B in FIG. 28. As shown in the figures, a ring-shaped illuminance distribution is formed.

Since this shape is the same as annular illumination, the same effect as that of the annular illumination will be obtained. Alteration of the annular shape can be realized by changing the width of the oscillating mirrors. Moreover, by changing the size of the spot shape at a standstill state, a flat illumination that will illuminate the whole pupil can be realized. Since this spot shape depends on the magnification of the beam expander 8*a*, if the magnification of the expander 8*a* is increased, a larger spot size can be realized, and if it is decreased, a smaller annular shape can be realized. Changing the magnification of the beam expander 8*a* is feasible by switching over a plurality of expanders each having a different magnification. Alternatively, if the beam expander is chosen to be a zoom lens, a spot having an arbitrary magnification becomes feasible.

Figure 30:
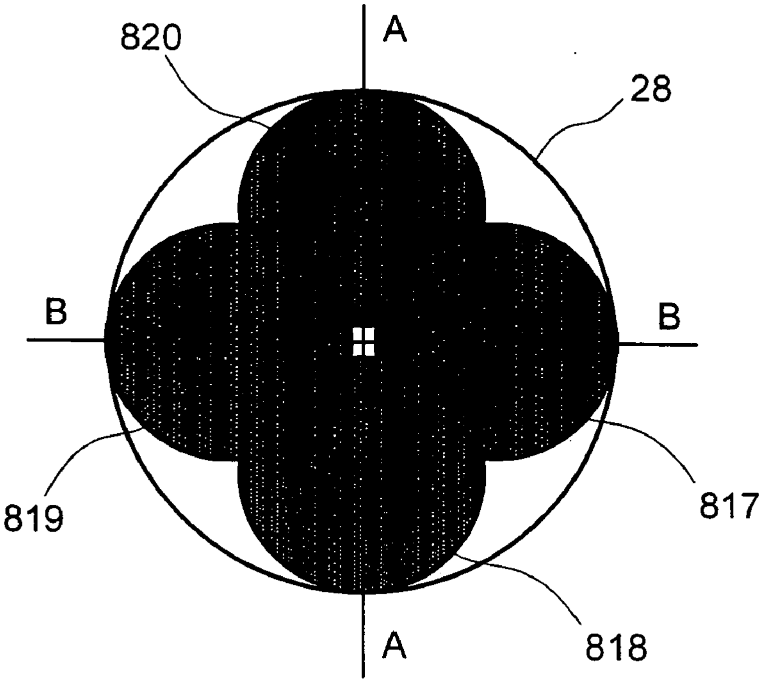
FIG. 30 is a diagram showing a situation where an operation of the oscillating mirror according to this invention on the pupil is observed.
Figure 31:
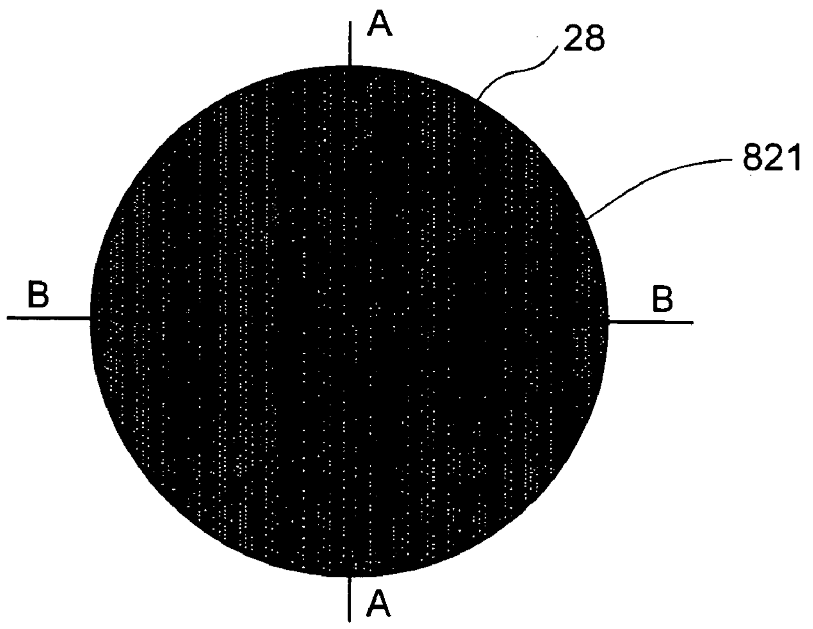
FIG. 31 is a diagram showing a situation where an operation of the oscillating mirror according to this invention on the pupil is observed.
Figure 32:
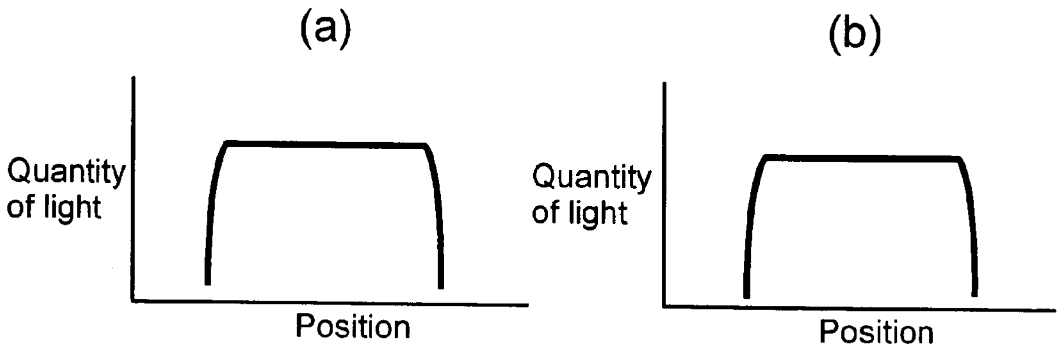
FIG. 32(*a*) and FIG. 32(*b*) are graphs illustrating an illuminance distribution on the pupil resulting from an operation of the oscillating mirror according to this invention, wherein FIG. 32(*a*) shows the distribution along line A-A in FIG. 31, and FIG. 32(*b*) shows the distribution along line B-B in FIG. 31.

One example in which the magnification of the beam expander is increased will be described. The same control as that of FIG. 26 is performed. FIG. 30 shows an image on the pupil 28 taken by the observation camera 32. The spot of illumination is located in the rightmost position 817 in the pupil 28 at time A in FIG. 26, in the lower most position 818 at time B, in the leftmost position 819 at time C, and in the uppermost position 820 at time D, respectively, the spot coming back to its original position after one cycle. FIG. 31 shows an image taken by the observation camera 32 when the mirrors are driven for one cycle. It becomes to have the shape of a spot 821. FIGS. 32(*a*) and 32(*b*) show the light intensity distribution of this spot 821 on the pupil 28 by the observation camera. FIG. 32(*a*) shows the light intensity distribution along the cross section A-A in FIG. 31, and FIG. 32(*b*) shows the light intensity distribution along the cross section B-B in FIG. 31. Uniform illumination all over the pupil 28 can be realized.

Figure 33:
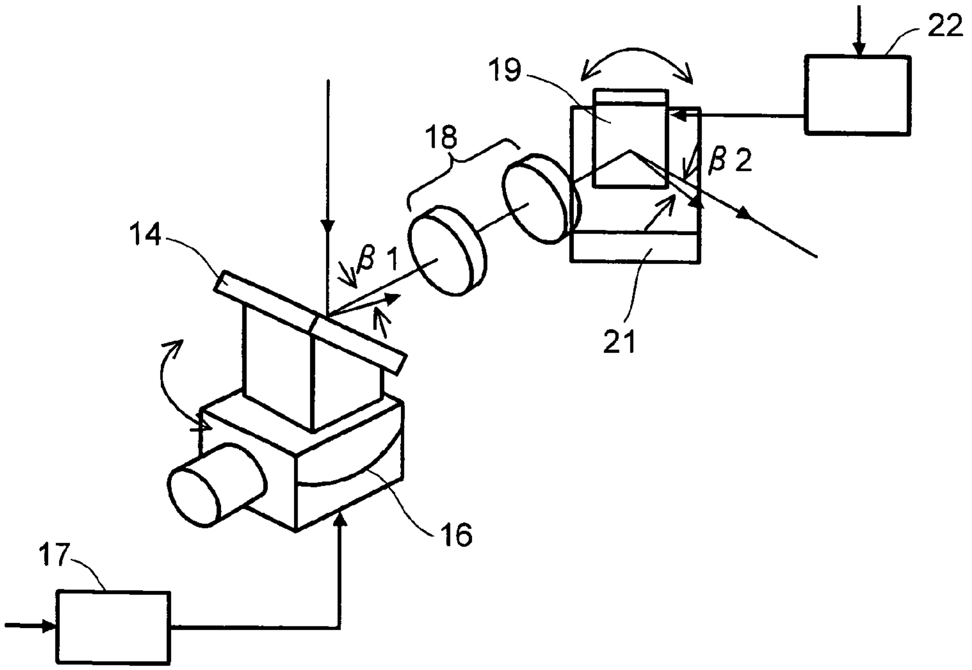
FIG. 33 is a diagram illustrating a goniometer according to this invention.
Figure 34:
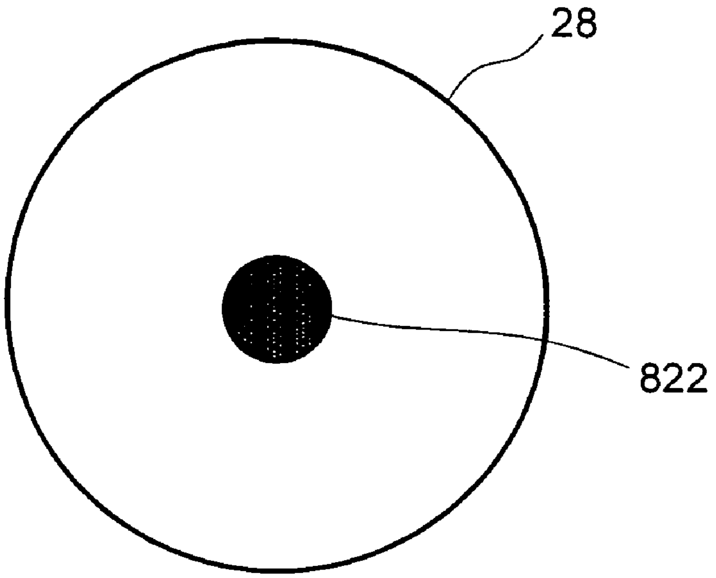
FIG. 34 is a diagram showing a situation where an operation by the goniometer according to this invention on the pupil is observed.

Next, oblique illumination will be described. The oblique illumination is feasible by controlling a goniometer on which the oscillating mirror is installed. FIG. 33 shows a detailed view of one example of an optical system in which oblique illumination is realized. This optical system has the same configuration as that of FIG. 14, but the oscillating mirrors are installed on goniometers, each of which can change its angle substantially in the same direction as the oscillating direction. The goniometers are arranged in a rockable manner, one in a vertical direction and the other in a horizontal direction. The vertical goniometer 16 can change the angle of a principal ray to angle β1 variably in response to the control circuit 17. The horizontal goniometer 21 can change the angle of the principal ray to angle β2 variably in response to the control circuit 22. Similarly, the oscillating mirrors 14, 19 are placed in the same conjugate positions by the use of the relay lens 18. Incidentally, since no current is fed to the oscillating mirrors 14, 19, they are in a stationary state in the center. FIG. 34 shows an image of the pupil 28 taken by the observation camera 32 when both goniometers are in the initial positions, that is, when the optical axis is not moved. A spot 822 of illumination is located in the center in the pupil 28. This state represents the usual epi-illumination.

Figure 35:
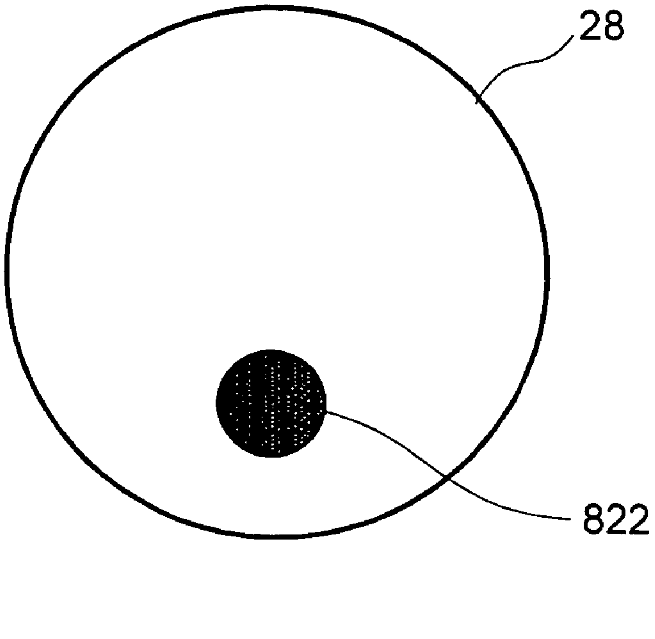
FIG. 35 is a diagram showing a situation where an operation by the goniometer according to this invention on the pupil is observed.
Figure 36:
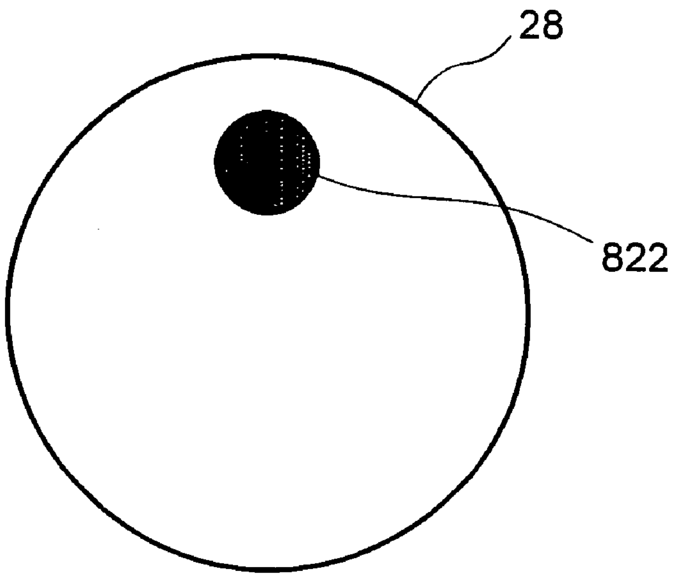
FIG. 36 is a diagram showing a situation where an operation by the goniometer according to this invention on the pupil is observed.

Next, a state in which the goniometer 16, which is capable of oscillating in the vertical direction, was moved, will be described. When β1 is moved upward in FIG. 33, the spot 822 is located on the lower side in the pupil 28, as shown in FIG. 35. Moreover, when β1 is moved downward in FIG. 33, the spot 822 is located on the upper side in the pupil 28, as shown in FIG. 36.

Figure 37:
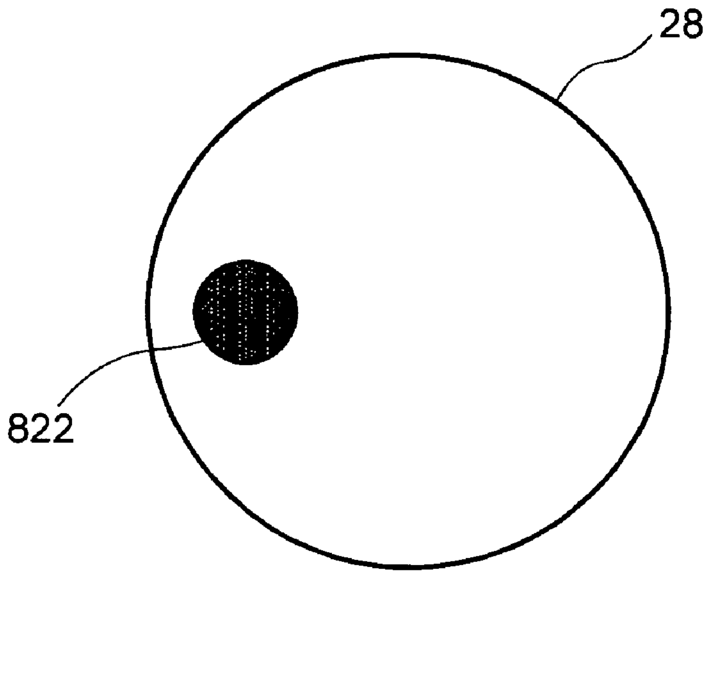
FIG. 37 is a diagram showing a situation where an operation by the goniometer according to this invention on the pupil is observed.
Figure 38:
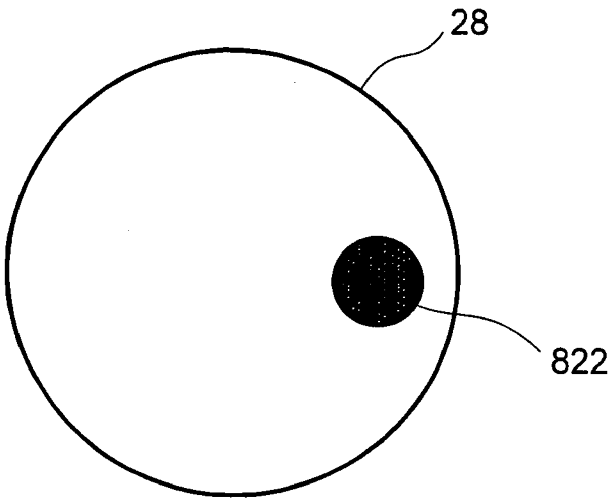
FIG. 38 is a diagram showing a situation where an operation by the goniometer according to this invention on the pupil is observed.

Similarly, a state in which the goniometer 21, which is capable of oscillating in the horizontal direction, was moved, will be described. When β2 is moved in the right direction in FIG. 33, the spot 822 is located on the left side in the pupil 28, as shown in FIG. 37. When β1 is moved downward in FIG. 33, the spot 822 is located on the right side in the pupil 28, as shown in FIG. 38.

Thus, making the principal ray illuminate the pupil obliquely realizes an oblique illumination. A combination of the positions of the two goniometers enables the setting of various angles.

Figure 39:
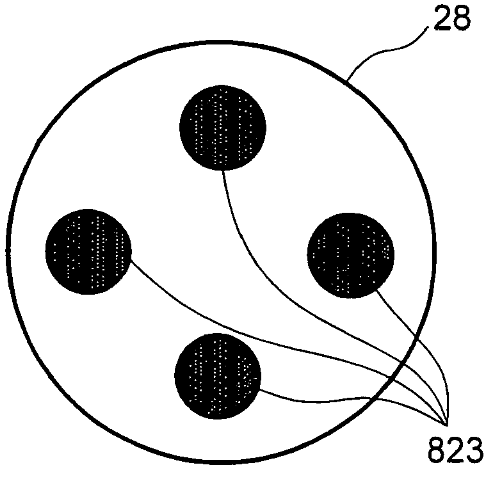
FIG. 39 is a diagram showing a situation where a quadruple according to this invention on the pupil is observed.
Figure 40:
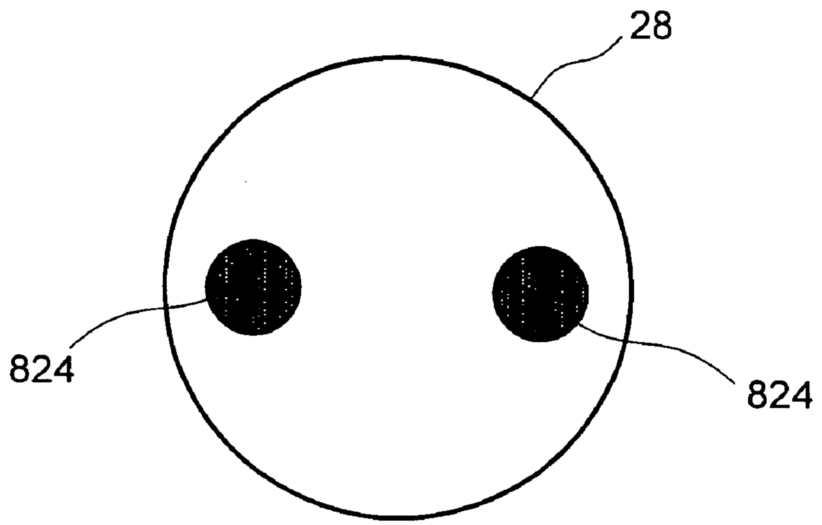
FIG. 40 is a diagram showing a situation where a duplex pole according to this invention on the pupil is observed.
Figure 41:
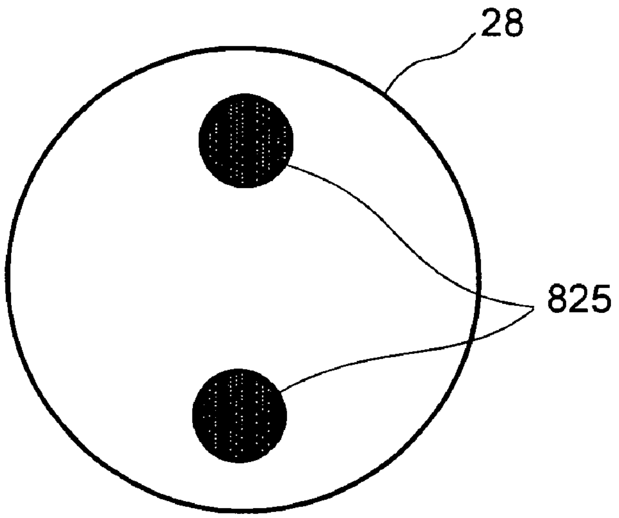
FIG. 41 is a diagram showing a situation where a duplex pole according to this invention on the pupil is observed.

Moreover, it is natural that a combination of the oscillating mirrors and the goniometers can realize a quadruple illumination, as shown FIG. 39, and duplex pole illuminations, as shown in FIG. 40 and FIG. 41. Note that these figures are images in the position of the pupil.

Note that the direction in which the principal ray moves when the resonance mirrors and the goniometers are controlled and the direction of the pupil at the observation camera does not necessarily coincide with the directions in this embodiment, and, needless to say, various modifications are possible.

In addition, it is needless to say that such an illumination method can be realized using various light shielding filters located in a position conjugate to the pupil until reaching the objective lens. For example, if a light shielding filter that matches the annular shape is used, the annular illumination can be realized in a pupil position as with this embodiment. Moreover, the annular illumination can be realized by a method whereby the light intensity in the central part is spread out to the peripheral part using something like a cone lens that is a combination of conical lenses following the beam expander 8*a*, instead of the beam shaper 9.

Figure 42:
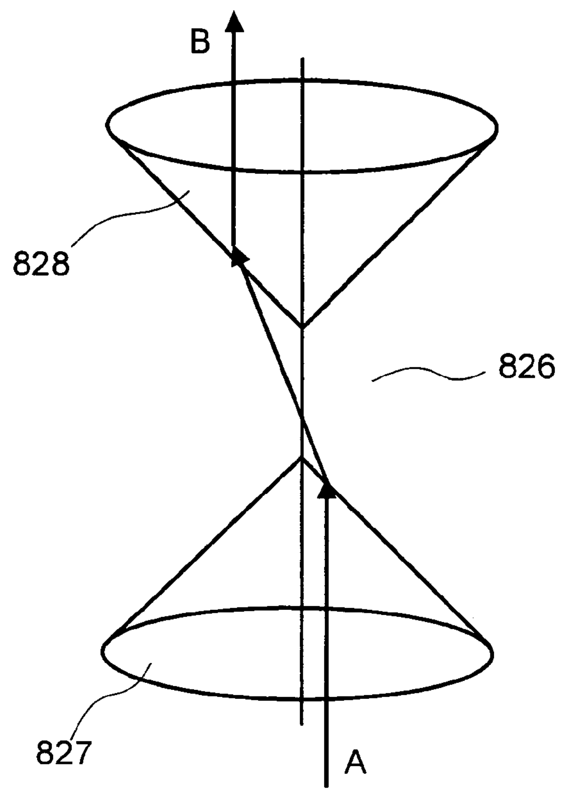
FIG. 42 is a diagram illustrating a cone lens according to this invention.
Figure 43:
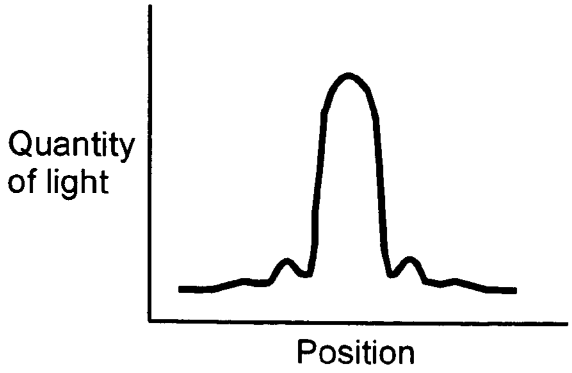
FIG. 43 is a graph illustrating an illuminance distribution of light entering the cone lens according to this invention.
Figure 44:
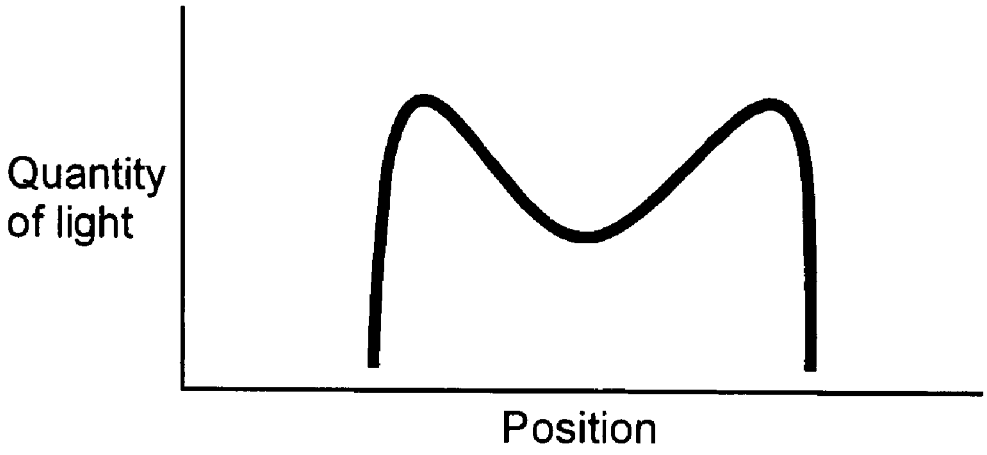
FIG. 44 is a graph illustrating an illuminance distribution of light emitting from the cone lens according to this invention.

FIG. 42 shows a conceptual diagram of a cone lens. The cone lens 826 is a counter arrangement of conical lenses 827, 828 disposed in an apex-to-apex manner. FIG. 43 shows an Illuminance distribution of incident light. The horizontal axis represents beam position, and the vertical axis represents light intensity. The obtained intensity distribution is a center-peaked shape, as shown in the figure. Representing the incident light entering in the vicinity of the center of the conical lens 827 by A, the light A is refracted by the conical lens 827, enters the edge of the conical lens 828, and is emitted as outgoing light B. FIG. 44 shows an illuminance distribution of outgoing light. The horizontal axis represents beam position, and the vertical axis represents light intensity. The obtained intensity distribution assumes a periphery-peaked shape, as shown in the figure, thus realizing the annular illumination. However, it is evident that both have fixed illumination shapes, and the light intensity is reduced to an insufficient level because the illumination light is shielded. However, if the illumination is used with its illumination range fixed, and the light intensity has some margin, and the decrease in the light intensity is not considered significant, such a configuration will not cause any problem.

Next, one example in which the focal position of the objective lens 27 is always set on the surface of the wafer 1 will be described. As seen in FIG. 1, an automatic focusing system 38 is installed in the neighborhood of the objective lens 27. It detects the height of the wafer 1 by a method not shown in the figure, measures the height with a height measurement circuit 39, and inputs the deviation of the height in the stage control circuit 3, whereby the Z stage 2*d* is controlled and, consequently, the height of the wafer 1 can always be adjusted.

These optical system constituents are arranged on the optical stand, not shown in the figure, in a discrete manner. On the optical stand, other optical systems, such as a light source, an illumination optical system, a detection optical system, and an image sensor, are fixed to constitute an integrated system. The optical stand takes the shape of, for example, a gate, and it is installed on a bench etc. on which the stage 2 is mounted in such an arrangement that it does not interfere with the range of movement of the stage 2. Therefore, it can perform detection which is stable relative to disturbances, such as a temperature change, vibration, etc.

Figure 45:
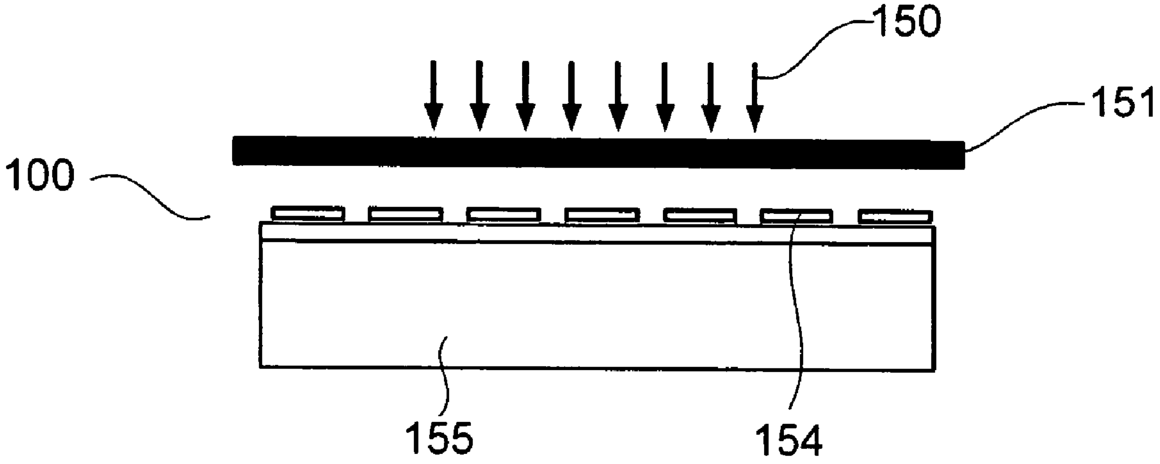
FIG. 45 is a diagram illustrating a TDI image sensor according to this invention.

Next, one example of the TDI sensor capable of detecting UV light, especially DUV light, in this way will be described. FIG. 45 shows a surface reflection type sensor. If a DUV laser light source is used as the illumination light source, it is necessary to use an image sensor having a sensitivity to DUV. Since, in a surface irradiation type image sensor 100, the incident light 150 is transmitted through a cover glass 151, passes through a gate 154, and enters CCD 155, incident light of a short wavelength attenuates; therefore, it has little sensitivity to wavelengths of not more than 400 nm and cannot detect DUV light effectively. To circumvent this problem, there is a method of detecting DUV light with an image sensor having a sensitivity only to visible light by forming an organic thin-film coating on cover glass and giving it a capability of emitting visible light when DUV light is incident thereon.

Figure 46:
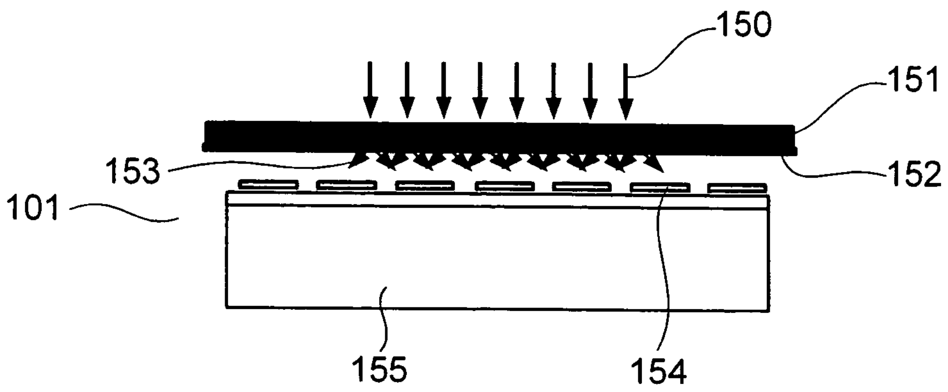
FIG. 46 is a diagram illustrating another TDI image sensor according to this invention.

FIG. 46 shows an image sensor of an organic thin-film coating system. Since an image sensor 101 of the organic thin-film coating system is such that an organic thin-film coating 152 is formed on the cover glass 151, and transmitted light of the incident light 150 emits fluorescent light 153 on the organic thin-film coating plane 152, even the surface irradiation type image sensor having a sensitivity only to visible light becomes capable of detecting DUV light.

Figure 47:
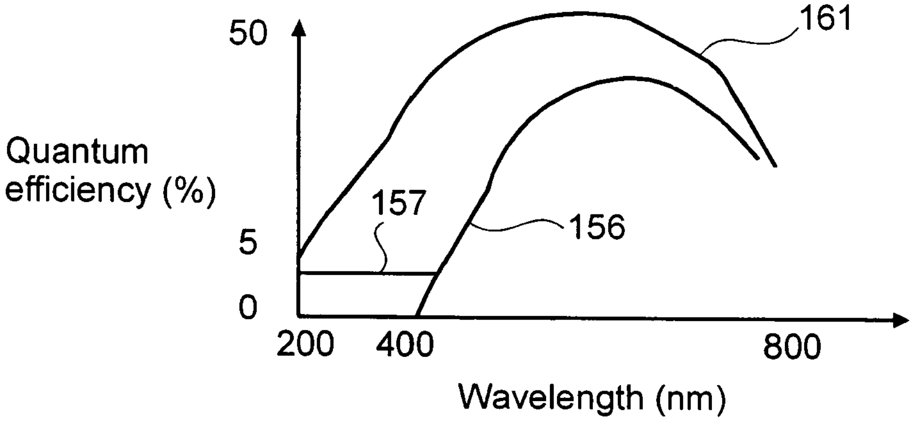
FIG. 47 is a graph illustrating a spectral characteristic of the TDI image sensor according to this invention.

FIG. 47 shows a spectral characteristic. The spectral characteristic 156 is a characteristic of the normal surface irradiation type image sensor 100. It has no sensitivity to wavelengths of not more than 400 nm. The spectral characteristic 157 is a characteristic of the image sensor 101 of the organic thin-film coating system. Adoption of the organic thin-film coating will add sensitivity to wavelengths of not more than 400 nm.

Figure 48:
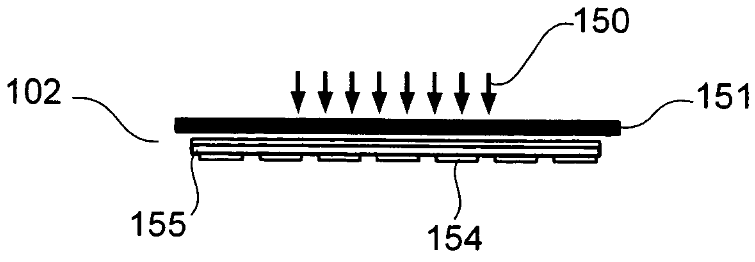
FIG. 48 is a diagram illustrating another TDI image sensor according to this invention.

Further, in order to enhance the sensitivity to DUV light, what is necessary is just to use a backside illumination type image sensor instead. FIG. 48 shows an example of the structure of the backside illumination type image sensor. In a backside illumination type image sensor 102, the incident light 150 is transmitted through the cover glass 151, and it enters a backside having no gate structure. Therefore, since light does not pass through the gate 154, it has a spectral characteristic 161, as shown in FIG. 47, that is, having a high quantum efficiency (for example, more than 30%), a large dynamic range (for example, more than 3000), and a sensitivity to wavelengths of not more than 400 nm. Therefore, it is especially advantageous for short wavelength illumination of less than 200 nm. With such an image sensor, only one image sensor can support several illumination wavelengths. Moreover, selection of the TDI image sensor leads to larger sensitivity. Furthermore, by giving it a characteristic of anti-blooming, a problem in which, when a light intensity more than necessary is obtained, electric charges overflow to surrounding pixels, can be solved. Thus, it is desirable to use an image sensor having the best quantum efficiency to a wavelength at the time of inspection.

Figure 49:
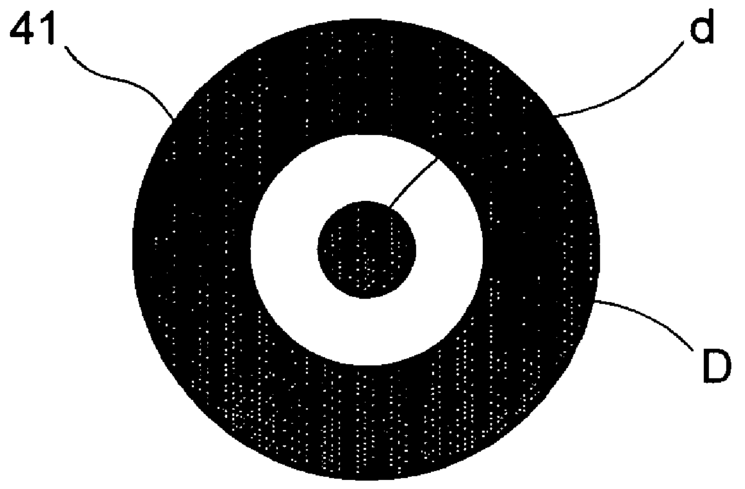
FIG. 49(*a*) and FIG. 49(*b*) are diagrams illustrating a pupil filter according to this invention.
Figure 49:
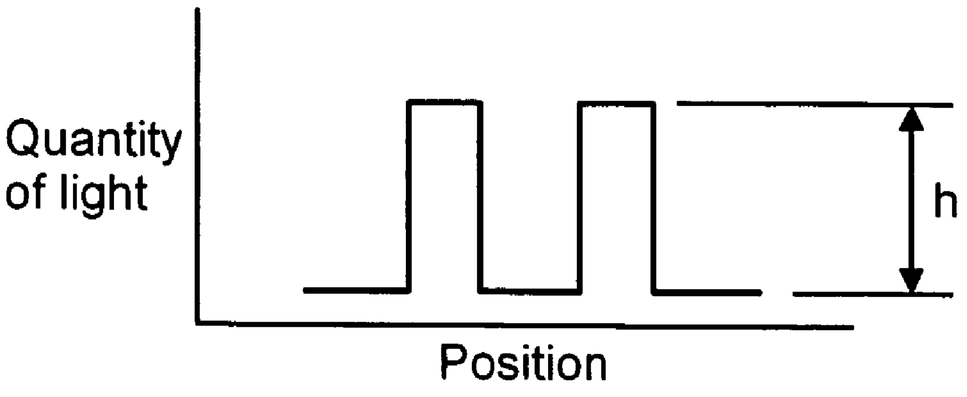

Next, the pupil filter 41 will be described. FIG. 49(*a*) show a diagram of the pupil filter 41. FIG. 49(*b*) shows one example of the transmissivity thereof. In FIG. 49(*a*), there is a light shielding part d in the center and a light shielding part D in the periphery. These light shielding parts change the transmissivities of the light shielding part d in the center and of the light shielding part D in the periphery. Several kinds of filters, each of which has a combination of different shape and transmissivity, are mounted on the apparatus, and the most optimal conditions shall be found according to a sample. Moreover, if phase conditions are added to this pupil filter 41, it will become capable of the changing detection conditions.

The operation of the configuration described above will now be described. At the time of inspection, the wafer 1 is moved at a uniform velocity by scanning the stage 2; at the same time, the position in the Z-direction of the surface to be inspected of the wafer 1 is always detected by the automatic focusing system 38 by a method not shown in the figure, and the Z stage 2*d* is controlled in the Z-direction so that the spacing between itself and the objective lens 27 becomes constant. The image sensor 35 detects brightness information of an inspection pattern formed on the wafer 1 (gray-scale image signal) with high precision. In the process of the wafer 1, since it is made of various materials and has various surface shapes, defect parts have various shapes. Therefore, as described above, it becomes possible to find conditions whereby a desired defect can be extracted through condition setting and result finding by detecting it with varied illumination conditions. That is, conditions whereby a defect part can be actualized can easily be set depending on the irradiation direction to that defect. Moreover, by changing the transmissivity and phase conditions of the filter 41 on the detection side, information of the actualized defect part can be further improved.

Figure 50:
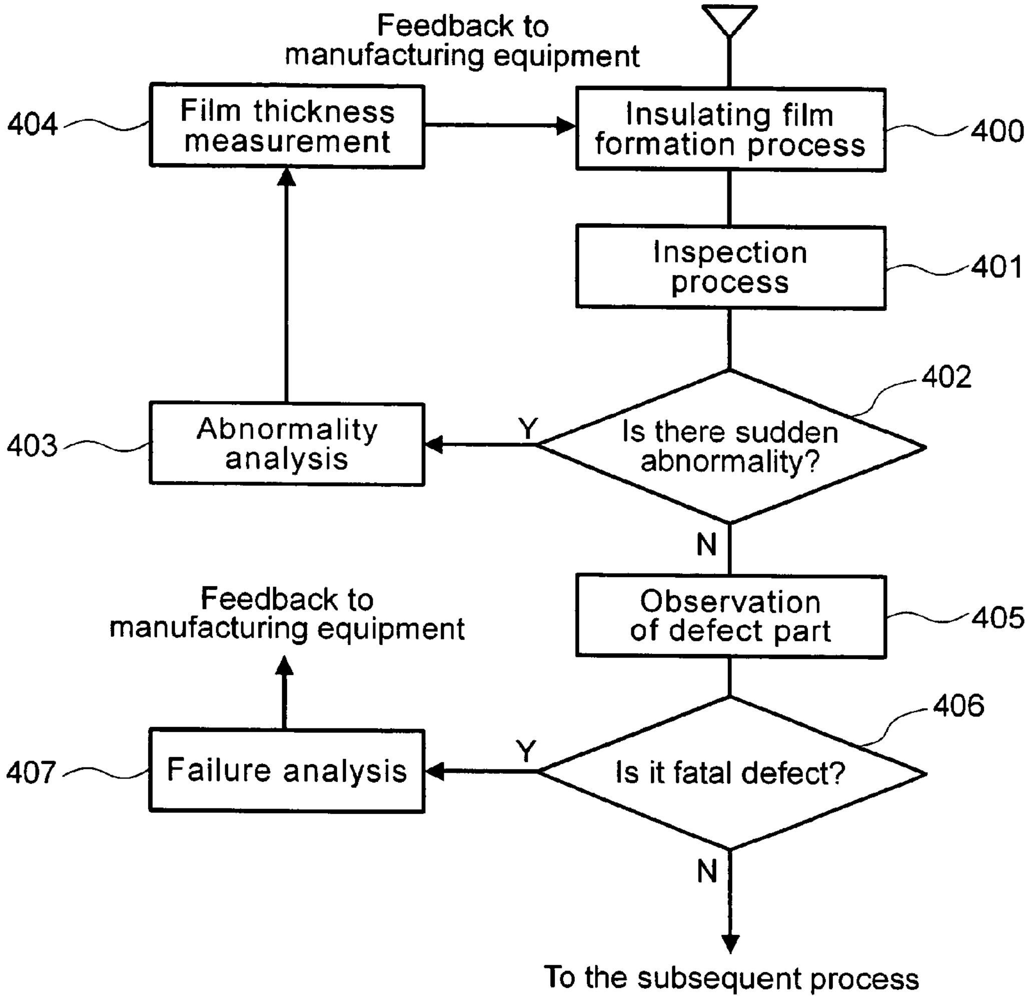
FIG. 50 is a flow diagram illustrating the flow in which the inspecting apparatus according to this invention is used.

FIG. 50 shows an effective method of applying the apparatus for inspecting a defect that was described in connection with this embodiment in a semiconductor formation process. Semiconductors, such as LSI, are formed through various processes. That is, a pattern delineated in each process is laminated to make a device. If there is even one defect, such as breaking of a wire and a short circuit, in any one of the processes, the device will be manufactured as a failure in the subsequent processes. Using this inspection apparatus, the presence of sudden abnormalities can be acquired and analyzed, which enables, for example, feedback to a film thickness apparatus (Steps 400 to 404). Moreover, failure analysis is performed by observing a detected defect part. If it is not a fatal defect, the device under manufacture is made to go through the rest of the processes, whereby the percent of defective parts can be reduced. If it is checked to be a defective, the information is fed back to manufacturing equipment without delay, whereby the manufacturing equipment is prevented from producing a mass of defective parts (Steps 405 to 407).

Figure 51:
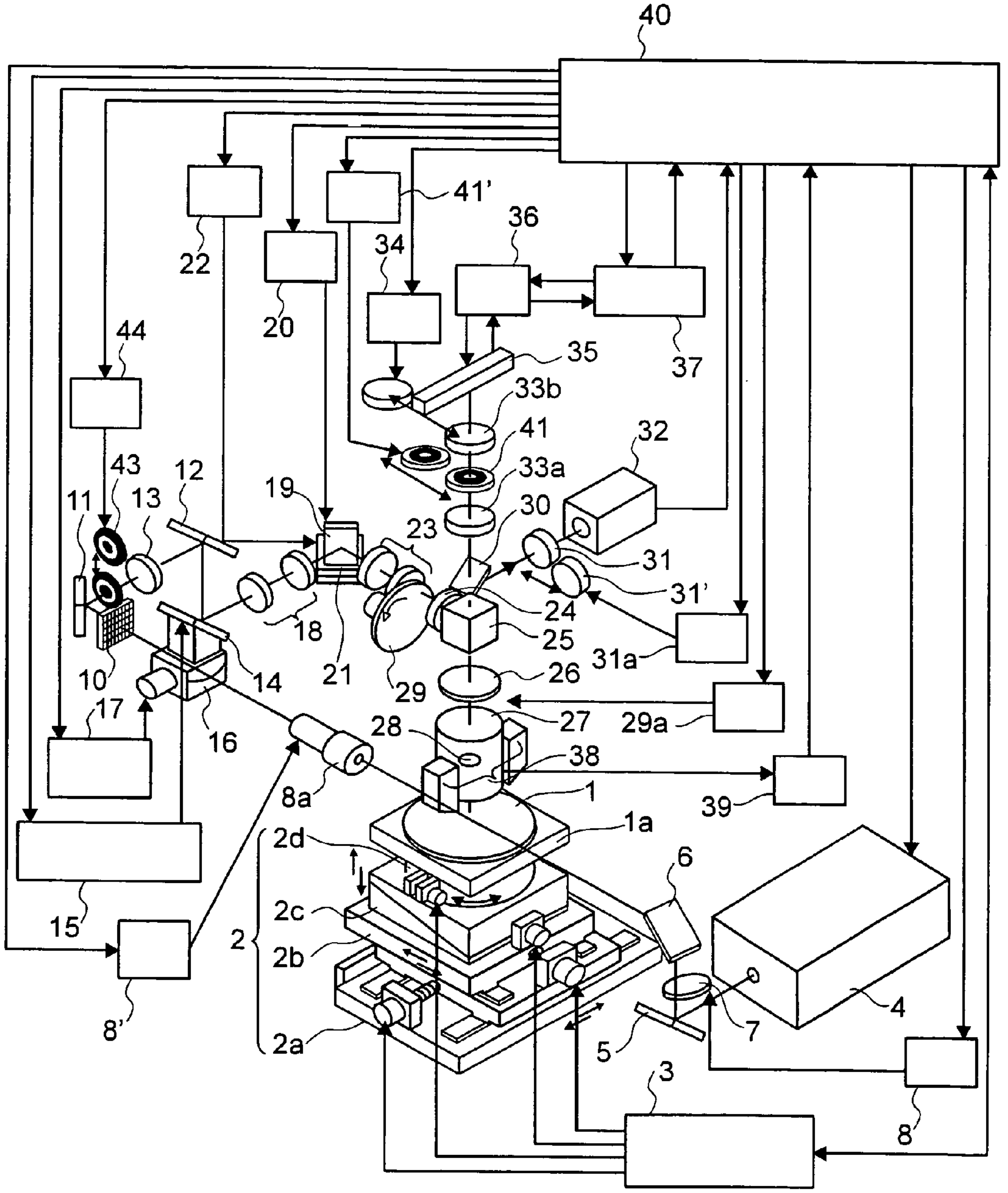
FIG. 51 is a block diagram showing another embodiment of the apparatus for inspecting an inspection pattern according to this invention.

FIG. 51 shows another embodiment. This embodiment is one example in which an illumination limiting filter 43 is installed in a position conjugate to the pupil 28 of the objective lens 27, and, consequently, the illumination conditions can be changed. It is possible that a plurality of the illumination limiting filters 43 are installed, and an illumination limiting filter control circuit 44 selects any one of the filters 43 by a method not shown in the figure. Other aspects of the configuration, except for the illumination limiting filter 43, are the same as those of FIG. 1. Detection of a defect by changing the illumination limiting filter 43 makes it possible to find conditions whereby a desired defect is extracted through condition setting and result finding.

Figure 52:
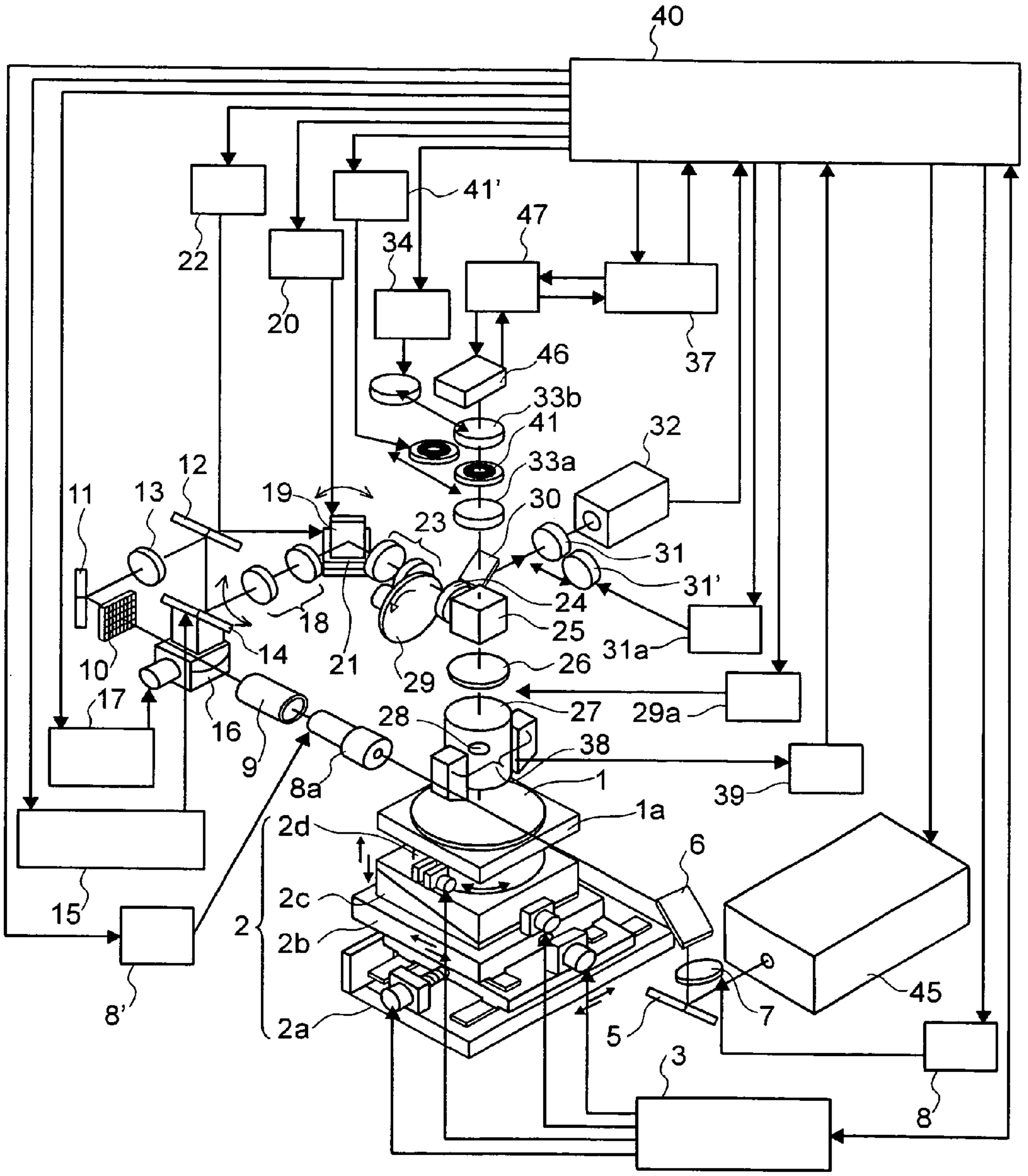
FIG. 52 is a block diagram showing further embodiment of the apparatus for inspecting an inspection pattern according to this invention.

FIG. 52 shows still another embodiment. This embodiment is an example in which the one-dimensional image sensor is replaced by a camera. A camera 46 is controlled by a controller 47. An image taken by the camera 46 is sent to the image processing unit 37. Other aspects of the configuration are the same as those of FIG. 1. During inspection, even for continuous operations of the stage 2 or when each step of the operation is performed within a shutter time of the camera 46, a similar image can be acquired. As this time, preferably, the frequency of the oscillating mirrors is synchronized with the shutter time of the camera 46.

Moreover, in connection with the previous embodiment, a bright field optical system was explained. However, if the configuration of a concentric microscope is used for the detection optical system, the same effect can be obtained.

The use of the apparatus for inspecting a pattern defect configured as in the foregoing description makes the following possible: an ultraviolet laser beam whose coherence was reduced is irradiated onto the surface of the wafer; an image of the surface of the wafer irradiated with this ultraviolet laser beam is taken up to obtain an image signal; and this image signal is processed, whereby a defect not more than 100 nm in size on the wafer can be detected and information on the position of this detected defect not more than 100 nm in size can be outputted.

Moreover, an ultraviolet laser beam whose coherence was reduced is irradiated onto a wafer having a diameter as large as 300 mm, an image of this wafer thus irradiated is taken up to detect an image of the wafer, and this detected image of the wafer is processed, whereby a defect not more than 100 nm in size of the pattern formed on the wafer can be detected at a throughput of three sheets per hour or more.

Especially, if this apparatus for inspecting a pattern is used for manufacture of a semiconductor device, it becomes possible to inspect a pattern of a design rule of 70 nm or less and to manufacture such a semiconductor device.

The invention may be embodied in other specific forms without departing from the spirit or essential characteristics thereof. The present embodiment is therefor to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An apparatus for inspecting a pattern, comprising:

a light source for emitting an ultraviolet laser beam;

light-intensity adjusting means for adjusting light intensity of the ultraviolet laser beam emitted from the light source;

coherence reducing means for reducing coherence of the ultraviolet laser beam whose light intensity was adjusted by the light-intensity adjusting means;

illumination means for irradiating the ultraviolet laser beam whose coherence was reduced by the coherence reducing means onto a sample;

diffracted-light controlling means for controlling diffracted light from the sample irradiated with the ultraviolet laser beam by the illumination means;

focusing means for focusing reflected light from the sample whose diffracted light was controlled by the diffracted-light controlling means into an image of the sample;

image detecting means for imaging the sample formed by the focusing means and detecting the image signal; and defect detecting means for detecting a defect of a pattern formed on the sample by processing the image signal detected by the image detecting means;

wherein the illumination means includes an objective lens through which the ultraviolet light is irradiated onto the sample, the illumination means enabling formation of at least one of an annular illumination, a quadruple spot illumination and a duplex spot illumination at a position of a pupil of the objective lens.

2. The apparatus for inspecting a pattern according to claim 1, wherein the image detecting means is configured to be equipped with the time-delay and integration type (TDI) image sensor having sensitivity to ultraviolet light, and the time-delay and integration type (TDI) image sensors is an anti-blooming TDI sensor and at the same time a backside illumination type TDI sensor whose cover glass is coated with an organic thin-film coating.

3. The apparatus for inspecting a pattern according to claim 1, wherein the defect detecting means outputs information on a position and dimensions of a detected defect of the pattern.

4. An apparatus for inspecting a pattern, comprising:

an illumination light source for emitting an ultraviolet laser beam;

light-intensity adjusting means for adjusting the light intensity of the ultraviolet laser beam emitted from the light source;

illumination means for irradiating the ultraviolet laser beam whose light intensity was adjusted by the light-intensity adjusting means onto a sample through an objective lens;

focusing means for focusing reflected light from the sample illuminated with the ultraviolet light by the illumination means into an image of the sample through the objective lens;

image detecting means for imaging the sample formed by the imaging means and detecting an image signal; and defect detecting means for detecting a defect of a pattern formed on the sample by processing a detection image signal detected by the image detecting means;

wherein the illumination means irradiates the ultraviolet light whose light intensity was adjusted onto the sample and the illumination means enables formation of at least one of an annular illumination, a quadruple spot illumination, and a duplex spot illumination at a position of a pupil of the objective lens, the imaging means has a backside illumination type TDI sensor, and the backside illumination type TDI sensor detects an image of the sample illuminated by the illumination means.

5. The apparatus for inspecting a pattern according to claim 4, further comprising a coherence reducing means for reducing coherence of the ultraviolet laser beam emitted from the illumination light source.

6. The apparatus for inspecting a pattern according to claim 5, wherein the illumination means has a scanning part for scanning the ultraviolet laser beam whose coherence was reduced by the coherence reducing means, in the position of the pupil of the objective lens.

7. The apparatus for inspecting a pattern according to claim 4, wherein the focusing means has a diffracted-light control part for controlling diffracted light from the sample that was irradiated with ultraviolet light by the illumination means.

8. An apparatus for inspecting a pattern, comprising:

an illumination light source;

light-intensity adjusting means for adjusting light intensity from the illumination light source;

illumination-range forming means for forming an illumination range of illumination light whose light intensity was adjusted by the light-intensity adjusting means;

coherence reducing means for reducing coherence of the illumination light emitted from the illumination-range forming means;

illumination means for changing the shape of a beam whose coherence was reduced by the coherence reducing means so as to enable formation of at least one of an annular shape, a quadruple spot shape, and a duplex spot shape at a position of a pupil of an objective lens for irradiation through the objective lens onto a sample for focusing;

focusing means for focusing reflected light from the sample irradiated by the illumination means, into an image;

diffracted-light controlling means for controlling diffracted light of the focusing means;

image detecting means for imaging the sample formed by the focusing means and detecting the image signal;

observation means for observing detection image detected by the image detecting means; and defect detecting means for detecting a defect of the pattern formed on the sample based on information on a detection image signal detected by the image detecting means.

9. The apparatus for inspecting a pattern according to claim 8, wherein the illumination light source is either a laser or a lump that emits light of a wavelength of 365 nm or less.

10. The apparatus for inspecting a pattern according to claim 8, wherein the light-intensity adjusting means includes a filter capable of decreasing the light intensity and a light intensity setting system capable of setting an arbitrary quantity of transmitted light by the filter, and the filter is arranged with its optical axis inclined so as not to directly return reflected light from the filter to the light source.

11. The apparatus for inspecting a pattern defect according to claim 8, wherein the illumination-range forming means is made up of rectangle illumination means for forming the illumination range into a rectangle;

the rectangle illumination means includes means for generating a plurality of light sources aligned in one direction on the pupil of the objective lens and means for generating a plurality of light sources orthogonal to the light sources; and the means for generating a plurality of light sources forms a rectangular illumination range on the sample by changing sizes of opposite sides.

12. The apparatus for inspecting a pattern defect according to claim 8, wherein the illumination means allows the beam to move freely and to stand still in the pupil, and is configured to move to a position conjugate to the sample.

13. The apparatus for inspecting a pattern defect according to claim 8, wherein the diffracted-light controlling means is installed in a position conjugate to the sample or its vicinity, a plurality of the focusing means each having a different magnification are installed, and one of them is selected and used.

14. The apparatus for inspecting a pattern defect according to claim 8, wherein the image detecting means is configured to be equipped with at least either a storage type image sensor or the time-delay and integration type (TDI) image sensor having sensitivity to ultraviolet light, the TDI image sensor being selected from: an anti-blooming TDI sensor; a surface irradiation type TDI sensor having a cover glass on which an organic thin-film coating is formed; and a backside illumination type TDI sensor.

15. The apparatus for inspecting a pattern defect according to claim 8, wherein the defect detecting means includes:

a storage part for storing a reference image signal;

a scatter-diagram preparation part for preparing a scatter diagram showing a corresponding relationship between features in a normal portion of the detection image signal detected by the image detecting means and features in a normal portion of the reference image signal stored in the storage part;

a gray-scale translation part for correcting gray-scale values of an image signal based on the scatter-diagram prepared by the scatter-diagram preparation part; and a defect detection part for detecting a defect of a pattern formed on the sample by comparing the detection image signal corrected in the gray-scale translation part and the reference image signal.

16. The apparatus for inspecting a pattern defect according to claim 8, wherein the defect detecting means is configured to output information on a position and dimensions of a detected pattern defect.

17. A method for inspecting a pattern, comprising the steps of:

adjusting light intensity of an ultraviolet laser beam emitted from a light source;

reducing coherence of the ultraviolet laser beam whose light intensity was adjusted;

irradiating the ultraviolet laser beam whose coherence was reduced onto a sample through an objective lens;

controlling diffracted light from the sample irradiated with the ultraviolet laser beam;

focusing reflected light from the sample whose diffracted light was controlled into an image;

imaging the formed image of the sample and detecting an image signal; and detecting a defect of a pattern formed on the sample by processing the detected image signal;

wherein in the step of irradiating, the ultraviolet laser beam is shaped into at least one of an annular shape, a quadruple spot shape, and a duplex spot shape at a position of a pupil of the objective lens.

18. The method for inspecting a pattern according to claim 17, wherein the formed image of the sample is imaged with a backside illumination type image sensor of a time-delay and integration type (TDI) having sensitivity to ultraviolet light.

19. The method for inspecting a pattern according to claim 17, wherein the method outputs information on a position and dimensions of the detected pattern defect.

20. A method for inspecting a pattern, comprising the steps of:

adjusting light intensity of ultraviolet light emitted from an illumination light source, irradiating the ultraviolet light whose light intensity was adjusted onto a sample through an objective lens, focusing reflected light from the sample illuminated with the ultraviolet light into an image through the objective lens;

imaging the formed image of the sample and detecting the image signal; and detecting a defect of the pattern formed on the sample by processing the detected image signal; in the step of irradiating, the ultraviolet light whose light intensity was adjusted onto the sample is shaped into at least one of an annular shape, a quadruple spot shape and a duplex spot shape at a position of a pupil of the objective lens, and in the step of imaging the sample and detecting an image signal, the image of the sample is detected with a backside illumination type TDI sensor.

21. The method for inspecting a pattern according to claim 20, wherein the ultraviolet light emitted from the illumination light source is an ultraviolet laser beam, and in the step of irradiating the ultraviolet light onto the sample, the ultraviolet laser beam is irradiated onto the sample after the coherence of the ultraviolet laser beam was reduced.

22. The method for inspecting a pattern according to claim 21, wherein in the step of irradiating the ultraviolet light onto the sample, the ultraviolet laser beam is irradiated onto the sample by scanning it on the pupil of the objective lens.

23. The method for inspecting a pattern according to claim 20, wherein in the step of focusing the reflected light from the sample into the image of the sample, the image is formed by controlling diffracted light from the sample irradiated with the ultraviolet light.

24. A method for inspecting a pattern defect, comprising the steps of:

irradiating an ultraviolet laser beam whose coherence is reduced onto the surface of a sample on which a pattern is formed;

imaging the surface of the sample irradiated with the ultraviolet laser beam and obtaining an image signal;

detecting a defect not more than 100 nm in size on the sample by processing the obtained image signal; and outputting information on a position of the detected defect not more than 100 nm in size on the sample;

wherein in the step of irradiating, the ultraviolet laser beam is irradiated onto the surface of the sample through an objective lens and the ultraviolet laser beam is shaped into at least one of an annular shape, a quadruple spot shape and a duplex spot shade at a position of a pupil of the objective lens.

25. The apparatus for inspecting a pattern according to claim 1, wherein the illumination means enables formation of at least one of the quadruple spot illumination and the duplex spot illumination at the position of the pupil of the objective lens.

26. The method for inspecting a pattern according to claim 17, wherein the ultraviolet laser beam is shaped into at least one of the quadruple spot shape and the duplex spot shape at the position of the pupil of the objective lens.

* * * * *